(12) United States Patent
Lee et al.

(10) Patent No.: US 8,473,044 B2
(45) Date of Patent: Jun. 25, 2013

(54) METHOD AND SYSTEM FOR MEASURING AND RANKING A POSITIVE OR NEGATIVE RESPONSE TO AUDIOVISUAL OR INTERACTIVE MEDIA, PRODUCTS OR ACTIVITIES USING PHYSIOLOGICAL SIGNALS

(75) Inventors: Hans C. Lee, Carmel, CA (US); Timmie T. Hong, San Diego, CA (US); William H. Williams, Hilo, HI (US); Michael R. Fettiplace, Madison, WI (US); Michael J. Lee, Carmel, CA (US)

(73) Assignee: The Nielsen Company (US), LLC, Schaumburg, IL (US)

( * ) Notice: Subject to any disclaimer, the term of this patent is extended or adjusted under 35 U.S.C. 154(b) by 1615 days.

(21) Appl. No.: 11/846,068

(22) Filed: Aug. 28, 2007

(65) Prior Publication Data

US 2008/0221472 A1 Sep. 11, 2008

Related U.S. Application Data

(60) Provisional application No. 60/905,181, filed on Mar. 7, 2007.

(51) Int. Cl.
*A61B 5/04* (2006.01)
(52) U.S. Cl.
USPC .......................................................... 600/544
(58) Field of Classification Search
USPC ................................................ 600/544, 545
See application file for complete search history.

(56) References Cited

U.S. PATENT DOCUMENTS

| | | | |
|---|---|---|---|
| 4,695,879 | A | 9/1987 | Weinblatt |
| 4,755,045 | A | 7/1988 | Borah et al. |
| 4,846,190 | A | 7/1989 | John |
| 4,931,934 | A | 6/1990 | Snyder |
| 4,974,602 | A | 12/1990 | Abraham-Fuchs et al. |
| 5,024,235 | A | 6/1991 | Ayers |
| 5,243,517 | A | 9/1993 | Schmidt et al. |
| 5,406,957 | A | 4/1995 | Tansey |
| 5,447,166 | A | 9/1995 | Gevins |

(Continued)

FOREIGN PATENT DOCUMENTS

| | | |
|---|---|---|
| EP | 1052582 | 11/2000 |
| EP | 1389012 | 2/2004 |

(Continued)

OTHER PUBLICATIONS

Sammler et al. ("Music and emotion: Electrophysiological correlates of the processing of pleasant and unpleasant music") Psychophysiology, 44 (2007), 293-304. Article first published online: Feb. 16, 2007.*

(Continued)

*Primary Examiner* — Patricia Mallari
*Assistant Examiner* — Christian Jang
(74) *Attorney, Agent, or Firm* — Hanley, Flight & Zimmerman, LLC

(57) ABSTRACT

A system and method for calculating a valence value captures an individual's positive or negative response to a media by considering alpha asymmetry of the individual's brain. This valence value can be used to compare media based on an individual or a group of individuals. Events of the media can be contrasted and compared by the valence value as well. Statistical measurements may be taken to improve media.

15 Claims, 10 Drawing Sheets

U.S. PATENT DOCUMENTS

| | | |
|---|---|---|
| 5,450,855 A | 9/1995 | Rosenfeld |
| 5,513,649 A | 5/1996 | Gevins et al. |
| 5,579,774 A | 12/1996 | Miller et al. |
| 5,601,090 A | 2/1997 | Musha |
| 5,649,061 A | 7/1997 | Smyth |
| 5,676,138 A | 10/1997 | Zawilinski |
| 5,692,906 A | 12/1997 | Corder |
| 5,724,987 A | 3/1998 | Gevins et al. |
| 5,740,812 A | 4/1998 | Cowan |
| 5,774,591 A | 6/1998 | Black et al. |
| 5,983,129 A | 11/1999 | Cowan et al. |
| 5,983,214 A | 11/1999 | Lang et al. |
| 6,001,065 A | 12/1999 | DeVito |
| 6,099,319 A | 8/2000 | Zaltman et al. |
| 6,254,536 B1 | 7/2001 | DeVito |
| 6,259,889 B1 | 7/2001 | LaDue |
| 6,292,688 B1 | 9/2001 | Patton |
| 6,309,342 B1 | 10/2001 | Blazey et al. |
| 6,322,368 B1 | 11/2001 | Young et al. |
| 6,349,231 B1 | 2/2002 | Musha |
| 6,425,764 B1 | 7/2002 | Lamson |
| 6,434,419 B1 | 8/2002 | Gevins et al. |
| 6,481,013 B1 | 11/2002 | Dinwiddie et al. |
| 6,585,521 B1 | 7/2003 | Obrador |
| 6,609,024 B1 | 8/2003 | Ryu et al. |
| 6,623,428 B2 | 9/2003 | Miller et al. |
| 6,626,676 B2 | 9/2003 | Freer |
| 6,648,822 B2 | 11/2003 | Hamamoto et al. |
| 6,652,283 B1 | 11/2003 | Van Schaack et al. |
| 6,656,116 B2 | 12/2003 | Kim et al. |
| 6,678,866 B1 | 1/2004 | Sugimoto et al. |
| 6,699,188 B2 | 3/2004 | Wessel |
| 6,792,304 B1 | 9/2004 | Silberstein |
| 6,839,682 B1 | 1/2005 | Blume |
| 6,978,115 B2 | 12/2005 | Whitehurst et al. |
| 7,035,685 B2 | 4/2006 | Ryu et al. |
| 7,050,753 B2 | 5/2006 | Knutson |
| 7,113,916 B1 | 9/2006 | Hill |
| 7,127,283 B2 | 10/2006 | Kageyama |
| D565,735 S | 4/2008 | Washbon |
| 7,383,728 B2 | 6/2008 | Noble et al. |
| 7,627,880 B2 | 12/2009 | Itakura |
| 7,689,272 B2 | 3/2010 | Farwell |
| 7,716,697 B2 | 5/2010 | Morikawa et al. |
| 7,739,140 B2 | 6/2010 | Vinson et al. |
| 7,742,623 B1 | 6/2010 | Moon et al. |
| 7,751,878 B1 | 7/2010 | Merkle et al. |
| 7,805,009 B2 | 9/2010 | Everett et al. |
| 7,853,122 B2 | 12/2010 | Miura et al. |
| 7,942,816 B2 | 5/2011 | Satoh et al. |
| 2001/0016874 A1 | 8/2001 | Ono et al. |
| 2001/0056225 A1 | 12/2001 | DeVito |
| 2002/0107454 A1 | 8/2002 | Collura et al. |
| 2002/0154833 A1 | 10/2002 | Koch et al. |
| 2002/0182574 A1 | 12/2002 | Freer |
| 2002/0188216 A1 | 12/2002 | Kayyali et al. |
| 2003/0003433 A1 | 1/2003 | Carpenter et al. |
| 2003/0055355 A1* | 3/2003 | Viertio-Oja ................. 600/544 |
| 2003/0063780 A1 | 4/2003 | Gutta et al. |
| 2003/0066071 A1 | 4/2003 | Gutta et al. |
| 2003/0076369 A1 | 4/2003 | Resner |
| 2003/0081834 A1 | 5/2003 | Philomin et al. |
| 2003/0093784 A1 | 5/2003 | Dimitrova et al. |
| 2003/0126593 A1 | 7/2003 | Mault |
| 2003/0153841 A1 | 8/2003 | Kilborn et al. |
| 2004/0018476 A1 | 1/2004 | Ladue |
| 2004/0039268 A1 | 2/2004 | Barbour et al. |
| 2004/0072133 A1 | 4/2004 | Kullok et al. |
| 2004/0077934 A1 | 4/2004 | Massad |
| 2004/0193068 A1 | 9/2004 | Burton et al. |
| 2004/0208496 A1 | 10/2004 | Pilu |
| 2004/0267141 A1 | 12/2004 | Amano et al. |
| 2005/0010087 A1 | 1/2005 | Banet |
| 2005/0010116 A1 | 1/2005 | Korhonen et al. |
| 2005/0043774 A1 | 2/2005 | Devlin et al. |
| 2005/0045189 A1 | 3/2005 | Jay |
| 2005/0066307 A1 | 3/2005 | Madhu et al. |
| 2005/0071865 A1 | 3/2005 | Martins |
| 2005/0096311 A1 | 5/2005 | Suffin et al. |
| 2005/0097594 A1 | 5/2005 | O'Donnell et al. |
| 2005/0113656 A1 | 5/2005 | Chance |
| 2005/0120372 A1 | 6/2005 | Itakura |
| 2005/0143629 A1 | 6/2005 | Farwell |
| 2005/0165285 A1 | 7/2005 | Iliff |
| 2005/0172311 A1 | 8/2005 | Hjelt et al. |
| 2005/0289582 A1 | 12/2005 | Tavares et al. |
| 2006/0064037 A1 | 3/2006 | Shalon et al. |
| 2006/0094970 A1 | 5/2006 | Drew |
| 2006/0111621 A1 | 5/2006 | Coppi et al. |
| 2006/0143647 A1 | 6/2006 | Bill |
| 2006/0217598 A1 | 9/2006 | Miyajima et al. |
| 2006/0258926 A1 | 11/2006 | Ali et al. |
| 2006/0277102 A1 | 12/2006 | Agliozzo |
| 2006/0293608 A1 | 12/2006 | Rothman et al. |
| 2006/0293921 A1 | 12/2006 | McCarthy et al. |
| 2007/0031798 A1 | 2/2007 | Gottfried |
| 2007/0048707 A1 | 3/2007 | Caamano et al. |
| 2007/0053513 A1 | 3/2007 | Hoffberg |
| 2007/0055169 A1 | 3/2007 | Lee et al. |
| 2007/0060830 A1 | 3/2007 | Le et al. |
| 2007/0060831 A1 | 3/2007 | Le et al. |
| 2007/0066914 A1 | 3/2007 | Le et al. |
| 2007/0116037 A1 | 5/2007 | Moore |
| 2007/0168461 A1 | 7/2007 | Moore |
| 2007/0173733 A1 | 7/2007 | Le et al. |
| 2007/0179396 A1 | 8/2007 | Le et al. |
| 2007/0184420 A1 | 8/2007 | Mathan et al. |
| 2007/0225585 A1 | 9/2007 | Washbon et al. |
| 2007/0235716 A1 | 10/2007 | Delic et al. |
| 2007/0238945 A1 | 10/2007 | Delic et al. |
| 2007/0265507 A1 | 11/2007 | De Lemos |
| 2008/0039737 A1* | 2/2008 | Breiter et al. ................. 600/544 |
| 2008/0091512 A1 | 4/2008 | Marci et al. |
| 2008/0144882 A1 | 6/2008 | Leinbach et al. |
| 2008/0159365 A1 | 7/2008 | Dubocanin et al. |
| 2008/0162182 A1 | 7/2008 | Cazares et al. |
| 2008/0177197 A1 | 7/2008 | Lee et al. |
| 2008/0211768 A1 | 9/2008 | Breen et al. |
| 2008/0218472 A1 | 9/2008 | Breen et al. |
| 2009/0024049 A1 | 1/2009 | Pradeep et al. |
| 2009/0024447 A1 | 1/2009 | Pradeep et al. |
| 2009/0024448 A1 | 1/2009 | Pradeep et al. |
| 2009/0024449 A1 | 1/2009 | Pradeep et al. |
| 2009/0024475 A1 | 1/2009 | Pradeep et al. |
| 2009/0025023 A1 | 1/2009 | Pradeep et al. |
| 2009/0030287 A1 | 1/2009 | Pradeep et al. |
| 2009/0030303 A1 | 1/2009 | Pradeep et al. |
| 2009/0030717 A1 | 1/2009 | Pradeep et al. |
| 2009/0030930 A1 | 1/2009 | Pradeep et al. |
| 2009/0036755 A1 | 2/2009 | Pradeep et al. |
| 2009/0036756 A1 | 2/2009 | Pradeep et al. |
| 2009/0062629 A1 | 3/2009 | Pradeep et al. |
| 2009/0062681 A1 | 3/2009 | Pradeep et al. |
| 2009/0063255 A1 | 3/2009 | Pradeep et al. |
| 2009/0063256 A1 | 3/2009 | Pradeep et al. |
| 2009/0082643 A1 | 3/2009 | Pradeep et al. |
| 2009/0083129 A1 | 3/2009 | Pradeep et al. |
| 2009/0105576 A1 | 4/2009 | Do et al. |
| 2009/0112077 A1 | 4/2009 | Nguyen et al. |
| 2009/0156925 A1 | 6/2009 | Jin et al. |
| 2009/0214060 A1 | 8/2009 | Chuang et al. |
| 2009/0222330 A1 | 9/2009 | Leinbach |
| 2010/0076333 A9 | 3/2010 | Burton et al. |

FOREIGN PATENT DOCUMENTS

| | | |
|---|---|---|
| EP | 1607842 | 12/2005 |
| JP | 07-329657 | 12/1995 |
| JP | 2002-000577 | 1/2002 |
| JP | 2002-344904 | 11/2002 |
| JP | 2003-016095 | 1/2003 |
| JP | 2003-111106 | 4/2003 |
| JP | 2003-178078 | 6/2003 |
| JP | 2006-0323547 | 11/2006 |
| JP | 2006-323547 | 11/2006 |
| KR | 10-2000-0072489 | 12/2000 |
| KR | 10-2001-0104579 | 11/2001 |

| | | |
|---|---|---|
| WO | 00/17824 | 3/2000 |
| WO | 01/97070 | 12/2001 |
| WO | 2007/019584 | 2/2007 |

OTHER PUBLICATIONS

Schmidt et al. (Frontal brain electrical activity (EEG) distinguishes valence and intensity of musical emotions) Cognition and Emotion, 2001, 15 (4), 487-500.*
Form PCT/ISA/220, PCT/US07/15019, "PCT Notification of Transmittal of the International Search Report and the Written Opinion of the International Searching Authority, or the Declaration," 1 pg.
Form PCT/ISA/210, PCT/US07/15019, "PCT International Search Report," 2 pgs.
Form PCT/ISA/237, PCT/US07/15019, "PCT Written Opinion of the International Searching Authority," 5 pgs.
Form PCT/IB/326, PCT/US07/015019, "Notification Concerning Transmittal of International Preliminary Report on Patentability."
Form PCT/IB/373, PCT/US07/15019, "International Preliminary Report on Patentability."
Form PCT/ISA/220, PCT/US07/14955, "PCT Notification of Transmittal of the International Search Report and the Written Opinion of the International Searching Authority, or the Declaration," 1 pg.
Form PCT/ISA/210, PCT/US07/14955, "PCT International Search Report," 2 pgs.
Form PCT/ISA/237, PCT/US07/14955, "PCT Written Opinion of the International Searching Authority," 6 pgs.
Form PCT/IB/326, PCT/US07/14955, "Notification Concerning Transmittal of International Preliminary Report on Patentability." 1 page.
Form PCT/IB/373, PCT/US07/14955, "International Preliminary Report on Patentability." 1 page.
Form PCT/ISA/220, PCT/US07/16796, "PCT Notification of Transmittal of the International Search Report and the Written Opinion of the International Searching Authority, or the Declaration," 1 pg.
Form PCT/ISA/210, PCT/US07/16796, "PCT International Search Report," 2 pgs.
Form PCT/ISA/237, PCT/US07/16796, "PCT Written Opinion of the International Searching Authority," 6 pgs.
Form PCT/IB/326, PCT/US07/16796, "Notification Concerning Transmittal of International Preliminary Report on Patentability." 1 page.
Form PCT/IB/373, PCT/US07/16796, "International Preliminary Report on Patentability." 1 page.
Form PCT/ISA/220, PCT/US06/31569, "PCT Notification of Transmittal of the International Search Report and the Written Opinion of the International Searching Authority, or the Declaration," 1 pg.
Form PCT/ISA/210, PCT/US06/31569, "PCT International Search Report," 3 pgs.
Form PCT/ISA/237, PCT/US06/31569, "PCT Written Opinion of the International Searching Authority," 6 pgs.
Form PCT/IB/326, PCT/US06/31569, "Notification Concerning Transmittal of International Preliminary Report on Patentability." 1 page.
Form PCT/IB/373, PCT/US06/31569, "International Preliminary Report on Patentability." 1 page.
Form PCT/ISA/220, PCT/US07/20714, "PCT Notification of Transmittal of the International Search Report and the Written Opinion of the International Searching Authority, or the Declaration," 1 pg.
Form PCT/ISA/210, PCT/US07/20714, "PCT International Search Report," 2 pgs.
Form PCT/ISA/237, PCT/US07/20714, "PCT Written Opinion of the International Searching Authority," 6 pgs.
Form PCT/IB/326, PCT/US07/20714, "Notification Concerning Transmittal of International.Preliminary Report on Patentability." 1 page.
Form PCT/IB/373, PCT/US07/20714, "International Preliminary Report on Patentability." 1 page.
Form PCT/ISA/220, PCT/US07/17764, "PCT Notification of Transmittal of the International Search Report and the Written Opinion of the International Searching Authority, or the Declaration," 1 pg.
Form PCT/ISA/210, PCT/US07/17764, "PCT International Search Report," 2 pgs.
Form PCT/ISA/237, PCT/US07/17764, "PCT Written Opinion of the International Searching Authority," 7 pgs.
Form PCT/IB/326, PCT/US07/17764, "Notification Concerning Transmittal of International Preliminary Report on Patentability." 1 page.
Form PCT/IB/373, PCT/US07/17764, "International Preliminary Report on Patentability." 1 page.
Form PCT/ISA/220, PCT/US07/20713, "PCT Notification of Transmittal of the International Search Report and the Written Opinion of the International Searching Authority, or the Declaration," 1 pg.
Form PCT/ISA/210, PCT/US07/20713, "PCT International Search Report," 2 pgs.
Form PCT/ISA/237, PCT/US07/20713, "PCT Written Opinion of the International Searching Authority," 5 pgs.
Form PCT/IB/326, PCT/US07/20713, "Notification Concerning Transmittal of International Preliminary Report on Patentability." 1 page.
Form PCT/IB/373, PCT/US07/20713, "International Preliminary Report on Patentability." 1 page.
Form PCT/ISA/220, PCT/US08/09110, "PCT Notification of Transmittal of the International Search Report and the Written Opinion of the International Searching Authority, or the Declaration," 1 pg.
Form PCT/ISA/210, PCT/US08/09110, "PCT International Search Report," 3 pgs.
Form PCT/ISA/237, PCT/US08/09110, "PCT Written Opinion of the International Searching Authority," 4 pgs.
Form PCT/ISA/220, PCT/US08/75640, "PCT Notification of Transmittal of the International Search Report and the Written Opinion of the International Searching Authority, or the Declaration," 1 pg.
Form PCT/ISA/210, PCT/US08/75640, "PCT International Search Report," 2 pgs.
Form PCT/ISA/237, PCT/US08/75640, "PCT Written Opinion of the International Searching Authority," 3 pgs.
Form PCT/ISA/220, PCT/US08/78633, "PCT Notification of Transmittal of the International Search Report and the Written Opinion of the International Searching Authority, or the Declaration," 1 pg.
Form PCT/ISA/210, PCT/US08/78633, "PCT International Search Report," 2 pgs.
Form PCT/ISA/237, PCT/US08/78633, "PCT Written Opinion of the International Searching Authority," 6 pgs.
Form PCT/ISA/220, PCT/US08/82147, "PCT Notification of Transmittal of the International Search Report and the Written Opinion of the International Searching Authority, or the Declaration," 1 pg.
Form PCT/ISA/210, PCT/US08/82147, "PCT International Search Report," 2 pgs.
Form PCT/ISA/237, PCT/US08/82147, "PCT Written Opinion of the International Searching Authority," 13 pgs.
Form PCT/ISA220, PCT/US08/82149, "PCT Notification of Transmittal of the International Search Report and the Written Opinion of the International Searching Authority, or the Declaration," 1 pg.
Form PCT/ISA/210, PCT/US08/82149, "PCT International Search Report," 2 pgs.
Form PCT/ISA/237, PCT/US08/82149, "PCT Written Opinion of the International Searching Authority," 14 pgs.
Form PCT/ISA/220, PCT/US08/75651, "PCT Notification of Transmittal of the International Search Report and the Written Opinion of the International Searching Authority, or the Declaration," 1 pg.
Form PCT/ISA/210, PCT/US08/75651, "PCT International Search Report," 2 pgs.
Form PCT/ISA/237, PCT/US08/75651, "PCT Written Opinion of the International Searching Authority," 9 pgs.
Form PCT/ISA/220, PCT/US08/85723, "PCT Notification of Transmittal of the International Search Report and the Written Opinion of the International Searching Authority, or the Declaration," 1 pg.
Form PCT/ISA/210, PCT/US08/85723, "PCT International Search Report," 2 pgs.
Form PCT/ISA/237, PCT/US08/85723, "PCT Written Opinion of the International Searching Authority," 7 pgs.
Form PCT/ISA/220, PCT/US08/85203, "PCT Notification of Transmittal of the International Search Report and the Written Opinion of the International Searching Authority, or the Declaration," 1 pg.
Form PCT/ISA/210, PCT/US08/85203, "PCT International Search Report," 2 pgs.

Form PCT/ISA/237, PCT/US08/85203, "PCT Written Opinion of the International Searching Authority," 6 pgs.
Form PCT/ISA/220, PCT/US08/75649, "PCT Notification of Transmittal of the International Search Report and the Written Opinion of the International Searching Authority, or the Declaration," 1 pg.
Form PCT/ISA/210, PCT/US08/75649, "PCT International Search Report," 3 pgs.
Form PCT/ISA/237, PCT/US08/75649, "PCT Written Opinion of the International Searching Authority," 5 pgs.
Technology Platform: SmartShirt + Eye-Tracking Innerscope Research, Mar. 2007.
Egner, Tobias; Emilie Strawson, and John H. Gruzelier, "EEG Signature and Phenomenology of Alpha/theta Neurofeedback Training Versus Mock Feedback." Applied Psychophysiology and Biofeedback. vol. 27, No. 4. Dec. 2002.
Clarke, Adam R. et al., EEG Analysis of Children with Attention-Deficit/Hyperactivity Disorder and Comorbid Reading Disabilities, Journal of Learning Disabilities, vol. 35, No. 3, (May-Jun. 2002), pp. 276-285.
Carter, R., "Mapping the Mind" 1998 p. 182 University of California Press, Berkley.
Harmony et al. (2004) Specific EEG frequencies signal general common cognitive processes as well as specific tasks processes in man. Int. Journal of Psychophysiology 53(3): 207-16.
Klimesch, W., Schimke, H., Schwaiger, J. (1994) Episodic and semantic memory: an analysis in the EEG theta and alpha band. Electroencephalography Clinical Neurophysiology.
Mizuhara, H., Wang LQ, Kobayashi, K., Yamaguchi, Y., (2004) A long range cortical network emerging with theta oscillation in mental task. Neuroreport 15(8): 1233-1238.
Selden, G (1981) "Machines that Read Minds." Science Digest, October.
Willis, M. & Hodson, V.; Discover Your Child's Learning Style: Children Learn in Unique Ways—Here's the Key to Every Child's Learning Success, Prime Publishing. Roseville, CA.
Wise, A (1996) The High Performance Mind, Mastering Brainwaves for Insight, Healing and Creativity. G.P. Putnam's Son, New York. pp. 13-15; 20-22; 143-156.
Wise, A (1996) The High Performance Mind, Mastering Brainwaves for Insight, Healing and Creativity. G.P. Putnam's Son, New York. pp. 156-158; 165-170; 186-187, 189-192.
El-Bab, M. (2001) Cognitive event related potentials during a learning task. Doctoral Dissertation, Faculty of Medicine, University of Southampton, UK.
Gevins et al. (1997) High resolution EEG mapping of cortical activation related to a working memory, Cereb Cortex. 7: 374-385.
Hughes, J.R. & John, E.R. (1999) Conventional and Quantitative Electroencephalography in Psychiatry. Journal of Neuropsychiatry and Clinical Neurosciences. vol. 11(2): 190-208.
The International Search report and Written Opinion for PCT Application PCT/US07/020713, Search report dated May 13, 2008, 8 pages (2008).
Notification of Grant of Patent Right for Invention, issued by the State Intellectual Property Office of the P.R. China, in connection with Chinese Patent Application No. 200780052869.9, on Aug. 31, 2012, 1 page.
Notification of the Third Office Action, issued by the State Intellectual Property Office of the P.R. China, in connection with Chinese Patent Application No. 200780052868.4, on Aug. 9, 2012, 7 pages.
Notification of the Second Office Action, issued by the State Intellectual Property Office of the P.R. China, in connection with Chinese Patent Application No. 200780052879.2, on May 4, 2012, 11 pages.
Notification of the Third Office Action, issued by the State Intellectual Property Office of the P.R. China, in connection with Chinese Patent Application No. 200680031159.3, on Mar. 28, 2012, 6 pages.
Notification of the Second Office Action, issued by the State Intellectual Property Office of the P.R. China, in connection with Chinese Patent Application No. 200680031159.3, on Oct. 19, 2011, 8 pages.
European Office Action, issued by the European Patent Office in connection with European Patent Application 07 838 838.6, on Sep. 5, 2012, 5 pages.
Supplemental European Search Report, issued by the European Patent Office in connection with European Patent Application No. 07796518.4, on Jul. 11, 2012, 8 pages.
European Office Action, issued by the European Patent Office in connection with European Patent Application No. 07 810 808.1, on Dec. 1, 2011, 6 pages.
Supplemental European Search Report, issued by the European Patent Office in connection with European Patent Appliation No. 06824810.3, on Nov. 22, 2011, 14 pages.
European Office Action, issued by the European Patent Office in connection with European Patent Application No. 07 852 430.3, on Mar. 6, 2012, 5 pages.
Supplemental European Search Report, issued by the European Patent Office in connection with European Patent Application No. 07811241.4, on Feb. 14, 2012, 6 pages.
European Office Action, issued by the European Patent Office in connection with European Patent Application No. 07 838 838.6, on Sep. 23, 2011, 4 pages.
Supplemental European Search Report, issued by the European Patent Office in connection with European Patent Application No. 06824810.3, on Nov. 3, 2011, 13 pages.
Supplemental European Search Report, issued by the European Patent Office in connection with European Patent Application No. 07796518.4, on Jul. 30, 2012, 9 pages.
Notification of Reason(s) for Rejection, issued by the Japanese Intellectual Property Office in connection with Japanese Patent Application No. JP2010-501190, on Oct. 2, 2012, 5 pages.
Notification of Reason(s) for Rejection, issued by the Japanese Intellectual Property Office in connection with Japanese Patent Application No. 2009-552658, on Apr. 19, 2012, 2 pages.
Notification of Reason(s) for Rejection, issued by the Japanese Intellectual Property Office in connection with Japanese Patent Application No. 2009-552657, on May 2, 2012, 5 pages.
Notification of Reason(s) for Rejection, issued by the Japanese Intellectual Property Office in connection with Japanese Patent Application No. 2009-552656, on Mar. 30, 2012, 3 pages.
Translation of an Office Action of Japan Patent Office, issued by the Japanese Intellectual Property Office in connection with Japanese Patent Application No. 2008-529085, Nov. 21, 2011, 2 pages.
Notice of Allowance and Fee(s) Due, issued by the United States Patent and Trademark Office in connection with U.S. Appl. No. 11/804,517, on Mar. 21, 2012, 8 pages.
Final Rejection, issued by the United States Patent and Trademark Office in connection with U.S. Appl. No. 11/804,517, on Sep. 1, 2011, 11 pages.
Office Action, issued by the United States Patent and Trademark Office in connection with U.S. Appl. No. 11/804,517, on Feb. 3, 2011, 15 pages.
Final Rejection, issued by the United States Patent and Trademark Office in connection with U.S. Appl. No. 11/804,517, on Jun. 23, 2010, 14 pages.
Office Action, issued by the United States Patent and Trademark Office in connection with U.S. Appl. No. 11/804,517, on Sep. 17, 2009, 15 pages.
Office Action, issued by the United States Patent and Trademark Office in connection with U.S. Appl. No. 11/804,555, on Mar. 15, 2012, 15 pages.
Final Rejection, issued by the United States Patent and Trademark Office in connection with U.S. Appl. No. 11/804,555, on Oct. 9, 2012, 11 pages.
Final Rejection, issued by the United States Patent and Trademark Office in connection with U.S. Appl. No. 11/804,555, on Jul. 21, 2010, 14 pages.
Office Action, issued by the United States Patent and Trademark Office in connection with U.S. Appl. No. 11/804,555, on Oct. 1, 2009, 17 pages.
Office Action, issued by the United States Patent and Trademark Office in connection with U.S. Appl. No. 11/779,814, on Feb. 13, 2012, 19 pages.
Final Rejection, issued by the United States Patent and Trademark Office in connection with U.S. Appl. No. 11/779,814, on Jun. 28, 2012, 18 pages.

Final Rejection, issued by the United States Patent and Trademark Office in connection with U.S. Appl. No. 11/779,814, on Jun. 18, 2010, 24 pages.
Office Action, issued by the United States Patent and Trademark Office in connection with U.S. Appl. No. 11/779,814, on Oct. 5, 2009, 24 pages.
Final Rejection, issued by the United States Patent and Trademark Office in connection with U.S. Appl. No. 11/500,678, on Dec. 8, 2010, 9 pages.
Office Action, issued by the United States Patent and Trademark Office in connection with U.S. Appl. No. 11/500,678, on Mar. 17, 2010, 10 pages.
Office Action, issued by the United States Patent and Trademark Office in connection with U.S. Appl. No. 11/500,678, on Sep. 3, 2008, 12 pages.
Final Rejection, issued by the United States Patent and Trademark Office in connection with U.S. Appl. No. 11/500,678, on , Jun. 9, 2009, 11 pages.
Final Rejection, issued by the United States Patent and Trademark Office in connection with U.S. Appl. No. 11/845,993, on Apr. 24, 2012, 8 pages.
Advisory Action, issued by the United States Patent and Trademark Office in connection with U.S. Appl. No. 11/845,993, on Jul. 20, 2012, 4 pages.
Office Action, issued by the United States Patent and Trademark Office in connection with U.S. Appl. No. 11/845,993, Aug. 4, 2011, 12 pages.
Final Rejection, issued by the United States Patent and Trademark Office in connection with U.S. Appl. No. 11/835,634, on Apr. 25, 2012, 23 pages.
Office Action, issued by the United States Patent and Trademark Office in connection with U.S. Appl. No. 11/835,634, on Sep. 1, 2011, 16 pages.
Final Rejection, issued by the United States Patent and Trademark Office in connection with U.S. Appl. No. 12/206,676, on Mar. 6, 2012, 9 pages.
Office Action, issued by the United States Patent and Trademark Office in connection with U.S. Appl. No. 12/206,676, on May 10, 2011, 9 pages.
Final Rejection, issued by the United States Patent and Trademark Office in connection with U.S. Appl. No. 12/206,702, on Jun. 3, 2010, 8 pages.
Office Action, issued by the United States Patent and Trademark Office in connection with U.S. Appl. No. 12/206,702, on May 28, 2009, 8 pages.
Final Rejection, issued by the United States Patent and Trademark Office in connection with U.S. Appl. No. 11/681,265, on Apr. 10, 2012, 18 pages.
Office Action, issued by the United States Patent and Trademark Office in connection with U.S. Appl. No. 11/681,265, on Jun. 21, 2011, 15 pages.
Adamic et al., "The political blogosphere and the 2004 U.S. election: Divided they blog," Proceedings WWW-2005 2nd Annual Workshop on the Weblogging Ecosystem, 2005, Chiba, Japan, 16 pages.
Adar et al., "Implicit structure and the dynamics of blogspace," Proceedings WWW-2004 Workshop on the Weblogging Ecosystem, 2004, New York, NY, 8 pages.
Aliod et al., "A Real World Implementation of Answer Extraction," Department of Computer Science, University of Zurich, Winterthurerstr. 190, CH-8057 Zurich, Switzerland, 6 pages.
Bishop, Mike, "ARROW Question/Answering Systems," Language Computer Corporation, 1999, 3 pages.
Bizrate, archived version of www.bizrate.com, Jan. 1999, 22 pages.
Blum, "Empirical Support for Winnow and Weighted-Majority Algorithms. Results on a Calendar Scheduling Domain," in Machine Learning, vol. 26, Kluwer Academic Publishers, Boston, USA, 1997, 19 pages.
Bournellis, Cynthia, "Tracking the hits on Web Sites," Communications International: vol. 22, Issue 9, London, Sep. 1995, 3 pages.
Chaum et al., "A Secure and Privacy-Protecting Protocol for Transmitting Personal Information Between Organizations," A.M. Odlyzko (Ed.): Advances in Cryptology, Crypto '86, LNCS 263, 1987, 51 pages.

Chaum, David L., "Untraceable Electronic Mail, Return Addresses, and Digital Pseudonymns," Communication of the ACM, vol. 24, No. 2, 1981, 5 pages.
Cohen, William W., "Data Integration using similarity joins and a word-based information representation language," ACM Transactions on Information Systems, vol. 18, No. 3, Jul. 2000, 34 pages.
Cohn et al., "Active Learning with Statistical Models," Journal of Artificial Intelligence Research 4, AI Access Foundation and Morgan Kaufmann Publishers, USA, 1996, 17 pages.
Dagan et al., "Mistake-Driven Learning in Text Categorization," in EMNLP '97, $2^{nd}$ Conference on Empirical Methods in Natural Language Processing, 1997, 9 pages.
Delahaye Group, "Delahaye Group to Offer Nets Bench: High Level Web-Site Qualitative Analysis and Reporting; NetBench Builds on Systems provided by I/PRO and Internet Media Services," 1995 Business Wire, Inc., May 31, 1995, 3 pages.
Dialogic, www.dialogic.com as archived on May 12, 2000, 34 pages.
Dillon et al., "Marketing research in a Marketing Environment," Times Mirror/Mosby College, USA, 1987, 5 pages.
EWATCH, eWatch's archived web site retrieved from [URL: http://web.archive.org/web/19980522190526/wwww.ewatch.com] on Sep. 8, 2004, archived May 22, 1998, 50 pages.
Egner et al., "EEG Signature and Phenomenology of Alpha/theta Neurofeedback Training Versus Mock Feedback," Applied Psychophysiology and Biofeedback, vol. 27, No. 4, Dec. 2002, 10 pages.
Farber, Dave, "IP: eWatch and Cybersleuth," retrieved from [URL: http://www.interesting-people.org/archives/interesting-people/200006/msg00090.html] Jun. 29, 2000, 4 pages.
Freund et al., "Selective Sampling Using the Query by Committee Algorithm," Machine Learning 28 Kluwer Academic Publishers, The Netherlands, 1997, 36 pages.
Glance et al., "Analyzing online disussion for marketing intelligence," Proceedings WWW-2005 2nd Annual Workshop on the Weblogging Ecosystem, Chiba, Japan, 2005, 2 pages.
Glance et al., "Deriving marketing intelligence from online discussion," 11th ACM SIGKDD International Conference on Knowledge Discovery and Data Mining, Chicago, IL, Aug. 21-24, 2005, 10 pages.
Grefenstette et al., "Validating the Coverage of Lexical Resources for Affect Analysis and Automatically Classifying New Words along Semantic Axes," Chapter X, 3, Mar. 2004, 16 pages.
Harabagiu, Sanda M., "An Intelligent System for Question Answering," University of Southern California; Modlovan, Dan, Southern Methodist University, 1996, 5 pages.
Harabagiu, Sanda M., "Experiments with Open-Domain Textual Question Answering," Department of Computer Science and Engineering at Southern Methodist Universtity, 2000, 7 pages.
Harabagiu, Sanda M., "Mining Textual Answers with Knowledge-Based Indicators," Department of Computer Science and Engineering at Southern Methodist University, 2000, 5 pages.
Housley et al., "Internet X.509 Public Key Infrastructure Certificate and CRL Profile," Network Working Group Request for Comments: 2459, Jan. 1999, 121 pages.
Joachims, Thorsten, "Text Categorization with Support Vector Machines: Learning with Many Relevant Features," in Machine Learning: ECML-98, Tenth European Conference on Machine Learning, 1998, 7 pages.
Kahn et al., "Categorizing Web Documents using Competitive Learning: An ingrediant of a Personal Adaptive Agent," IEEE 1997, 4 pages.
Katz, Boris, "From Sentence Processing to Information Access on the World Wide Web," MIT Artificial Intelligence Laboratory, Feb. 27, 1997, 20 pages.
Kleppner, "Advertising Procedure," 6th edition, 1977, Prentice-Hall, Inc., Englewood Cliffs, NJ, p. 492, 3 pages.
Kotler, "Marketing Management," PrenticeHall International Inc., Upper Saddle River, NJ, 1997, 10 pages.
Klimesch, "EEG alpha and theta oscillations reflect cognitive and memory performance: a review and analysis," Brain Research Reviews, vol. 29, 1999, 27 pages.

Lenz et al., "Question answering with Textual CBR," Department of Computer Science, Humboldt University Berlin, D-10099 Berlin, 1998, 12 pages.

Littlestone, Nick, "Learning Quickly When Irrelevant Attributes Abound: A New Linear-threshold Algorithm," in Machine Learning, vol. 2, Kluwer Academic Publishers, Boston, MA, 1988, 34 pages.

Marlow, "Audience, structure and authority in the weblog community," International Communication Association Conference, MIT Media Laboratory, New Orleans, LA 2004, 9 pages.

McCallum et al., "Text Classification by Bootstrapping with the Keywords, EM and Shrinkage," Just Research and Carnegie Mellon University, Pittsburgh, PA, circa 1999, 7 pages.

McLachlan et al., "The EM Algorithm and Extensions," John Wiley & Sons, Inc., New York, NY, 1997, 301 pages.

Moldovan et al., "LASSO: A Tool for Surfing the Answer Net," Department of Computer Science and Engineering at Southern Methodist University, 1999, 9 pages.

Nakashima et al., "Information Filtering for the Newspaper," IEEE 1997, 4 pages.

Nanno et al., "Automatic collection and monitoring of Japanese Weblogs," Proceedings WWW-2004 Workshop on the weblogging Ecosystem, 2004, New York, NY, 7 pages.

NETCURRENT, NetCurrent's web site, http://web.archive.org/web/20000622024845/www.netcurrents.com, retrieved on Jan. 17, 2005, archived on Jun. 22, 2000 and Sep. 18, 2000, 17 pages.

Pang et al., "Thumbs up? Sentiment Classification using Machine Learning Techniques," in Proceedings of EMNLP 2002, 8 pages.

Reguly, "Caveat Emptor Rules on the Internet," The Globe and Mail (Canada): Report on Business Column, Apr. 10, 1999, 2 pages.

Reinartz, "Customer Lifetime Value Analysis: An Integrated Empirical Framework for Measurement and Explanation," dissertation: Apr. 1999, 68 pages.

Soderland et al., "Customer Satisfaction and Links to Customer Profitability: An Empirical Examination of the Association Between Attitudes and Behavior," SSE/EFI Working Paper Series in Business Administration, Jan. 1999, 22 pages.

Thomas, "International Marketing," International Textbook Company, Scranton, PA 1971, 3 pages.

Trigaux, Robert, "Cyberwar Erupts Over Free Speech Across Florida, Nation," Knight-Ridder Tribune Business News, May 29, 2000, 4 pages.

Tull et al., "Marketing Research Measurement and Method," MacMillan Publishing Company, New York, NY, 1984, 9 pages.

Voorhees, Ellen M., "The TREC-8 Question Answering Track Report," National Institute of Standards and Technology, 1999, 6 pages.

Wiebe et al., "Identifying Collocations for Recognizing Opinions," in proceedings of ACL/EACL '01 Workshop on Collocation, Toulouse, France, Apr. 9, 2001, 9 pages.

Word of Mouth Research Case Study, "The Trans Fat Issue, Analysis of online consumer conversation to understand how the Oreo lawsuit impacted word-of-mouth on trans fats," Aug. 16, 2004, 35 pages.

Yang, "An Evaluation of Statistical Approaches to Text Categorization," Information Retrieval 1 (1/2) Apr. 10, 1999, 12 pages.

ZAGAT, www.zagat.com, archived on Apr. 29, 1999, 33 pages.

ZAGAT, www.zagat.com, archived version of p. 34, Feb. 1999, 1 page.

Notification of Reasons(s) for Rejection, issued by the Japanese Intellectual Property Office in connection with Japanese Patent Application No. 2009-552661, Nov. 13, 2012. 3 pages.

Notification of Reasons(s) for Rejection, issued by the Japanese Intellectual Property Office in connection with Japanese Patent Application No. 2009-552660, Nov. 16, 2012, 3 pages.

European office action, issued by the European Patent Office in connection with European application No. 07 852 430.3, on Feb. 6, 2013, 5 pages.

Notification of the Third Office Action, issued by the State Intellectual Property Office of the P.R. China, in connection with Chinese Patent Application No. 200780052879.2, on Dec. 31, 2012, 10 pages.

Notification of Reasons(s) for Rejection, issued by the Japanese Intellectual Property Office in connection with Japanese Patent Application No. 2009-552661, Nov. 13, 2012, 3 pages.

Notification of Reasons(s) for Rejection, issued by the Japanese Intellectual Property Office in connection with Japanese Patent Application No. 2009-552659, Nov. 16, 2012, 4 pages.

Notification of Reasons(s) for Rejection issued by the Japanese Intellectual Property Office in connection with Japanese Patent Application No. 2009-552660, Nov. 16, 2012, 3 pages.

Office Action, issued by the United States Patent and Trademark Office in connection with U.S. Appl. No. 12/835,714, on Jan. 22, 2013, 34 pages.

Form PCT/ISA/220, PCT/US07/15019, "PCT Notification of Transmittal of The International Search Report and the Written Opinion of the International Searching Authority, or the Declaration, " 1 pg., Jun. 11, 2008.

Form PCT/ISA/210, PCT/US07/15019, "PCT International Search Report, " 2 pgs., Jun. 11, 2008.

Form PCT/ISA/237, PCT/US07/15019, "PCT Written Opinion of the International Searching Authority, " 5 pgs., Jun. 11, 2008.

Form PCT/IB/326, PCT/US07/015019, "Notification Concerning Transmittal of International Preliminary Report on Patentability.", Sep. 17, 2008.

Form PCT/IB/373, PCT/US07/15019, "International Preliminary Report on Patentability.", Sep. 8, 2009.

Form PCT/ISA/237, PCT/US07/15019, "PCT Written Opinion of the International Searching Autority, " 5 pgs., Jun. 11, 2008.

Form PCT/ISA/220, PCT/US07/14955, "PCT Notification of Transmittal of The International Search Report and the Written Opinion of the International Searching Authority, or the Declaration, " 1 pg., Jul. 3, 2008.

Form PCT/ISA/210, PCT/US07/14955, "PCT International Search Report, " 2 pgs., Jul. 3, 2008.

Form PCT/ISA/237, PCT/US07/14955, "PCT Written Opinion of the International Searching Authority, " 6 pgs., Jul. 3, 2008.

Form PCT/IB/3226, PCT/US07/14955, "Notification Concerning Transmittal of International Preliminary Report on Patentability." 1 page, Sep. 17, 2009.

Form PCT/IB/373, PCT/US07/14955, "International Preliminary Report on Patentability." 1 page, Sep. 8, 2009.

Form PCT/ISA/220, PCT/US07/16796, "PCT Notification of Transmittal of The International Search Report and the Written Opinion of the International Searching Authority, or the Declaration, " 1 pg., Jul. 3, 2008.

Form PCT/ISA/210, PCT/US07/16796, "PCT International Search Report, " 2 pgs., Jul. 3, 2008.

Form PCT/ISA/237, PCT/US07/16796, "PCT Written Opinion of the International Searching Authority, " 6 pgs., Jul. 3, 2008.

Form PCT/IB/326, PCT/US07/16796, "Notification Concerning Transmittal of International Preliminary Report on Patentability. " 1 page, Sep. 17, 2009.

Form PCT/IB/373, PCT/US07/16796, "International Preliminary Report on Patentability." 1 page, Sep. 8, 2009.

Form PCT/ISA/237, PCT/US07/16796, "PCT Written Opinion of the International Searching Authority, " 6 pg., Jul. 3, 2008.

Form PCT/ISA/220, PCT/US06/31569, "PCT Notification of Transmittal of The International Search Report and the Written Opinion of the International Searching Authority, or the Declaration, " 1 pg., Feb. 20, 2007.

Form PCT/ISA/210, PCT/US06/31569, "PCT International Search Report, " 3 pgs., Feb. 20, 2007.

Form PCT/ISA/237, PCT/US06/31569, "PCT Written Opinion of the International Searching Authority, " 6 pgs., Feb. 20, 2007.

Form PCT/IB/326, PCT/US06/31569, "Notification Concerning Transmittal of International Preliminary Report on Patentability." 1 page, Mar. 13, 2008.

Form PCT/IB/373, PCT/US06/31569, "International Preliminary Report on the Patentability." 1 page, Mar. 4, 2008.

Form PCT/ISA/220, PCT/US07/20714, "PCT Notification of Transmittal of The International Search Report and the Written Opinion of the International Searching Authority, or the Declaration, " 1 pg., Apr. 8, 2008.

Form PCT/ISA/210, PCT/US07/20714, "PCT International Search Report, " 2 pgs., Apr. 8, 2008.

Form PCT/ISA/237, PCT/US07/20714, "PCT Written Opinion of the International Searching Authority, " 6 pgs., Apr. 8, 2008.

Form PCT/IB/326, PCT/US07/20714, "Notification Concerning Transmittal of International Preliminary Report on Patentability." 1 page, Sep. 17, 2009.
Form PCT/IB/373, PCT/US07/20714, "International Preliminary Report on Patentability." 1 page, Sep. 8, 2009.
Form PCT/ISA/220, PCT/US07/17764, "PCT Notification of Transmittal of The International Search Report and the Written Opinion of the International Searching Authority, or the Declaration, " 1 pg., May 6, 2008.
Form PCT/ISA/210, PCT/US07/17764, "PCT International Search Report, " 2 pgs., May 6, 2008.
Form PCT/ISA/237, PCT/US07/17764, "PCT Written Opinion of the International Searching Authority, " 7 pgs., May 6, 2008.
Form PCT/IB/326, PCT/US07/17764, "Notification Concerning Transmittal of International Preliminary Report on Patentability." 1 page, Sep. 17, 2009.
Form PCT/IB/373, PCT/US07/17764, "International Preliminary Report on Patentability." 1 page, Sep. 8, 2009.
Form PCT/ISA/220, PCT/US07/20713, "PCT Notification of Transmittal of The International Search Report and the Written Opinion of the International Searching Authority, or the Declaration, " 1 pg., May 13, 2008.
Form PCT/ISA/210, PCT/US07/20713, "PCT International Search Report, " 2 pgs., May 13, 2008.
Form, PCT/ISA/237, PCT/US07/20713, "PCT Written Opinion of the International Searching Authority, " 5 pgs., May 13, 2008.
Form PCT/IB/326, PCT/US07/20713, "Notification Concerning Transmittal of International Preliminary Report on Patentability." 1 page, Sep. 17, 2009.
Form PCT/IB/373, PCT/US07/20713, "International Preliminary Report on Patentability." 1 page, Sep. 8, 2009.
Form PCT/ISA/237, PCT/US07/20713, "PCT Written Opinion of the International Searching Authority, " 5 pgs., May 13, 2008.
Form PCT/ISA/220, PCT/US08/09110, "PCT Notification of Transmittal of The International Search Report and the Written Opinion of the International Search Authority, or the Declaration, " 1 pg., Feb. 20, 2009.
Form PCT/ISA/210, PCT/US08/09110, "PCT International Search Report, " pgs., Feb. 20, 2009.
Form PCT/ISA/237, PCT/US08/09110, "PCT Written Opinion of the International Searching Authority, " 4 pgs., Feb. 20, 2009.
Form PCT/ISA.220, PCT/US08/75640, "PCT Notification of Transmittal of The International Search Report and the Written Opinion of the International Searching Authority, or the Declaration, " 1 pg., Nov. 7, 2008.
Form PCT/ISA/210, PCT/US08/75640, "PCT International Search Report, " 2 pgs., Nov. 7, 2008.
Form PCT/ISA/237, PCT/US08/75640, "PCT Written Opinion of the International Searching Authority, " 3 pgs., Nov. 7, 2008.
Form PCT/ISA/220, PCT/US08/78633, "PCT Notification of Transmittal of The International Search Report and the Written Opinion of the International Searching Authority, or the Declaration, " 1 pg., Dec. 5, 2008.
Form PCT/ISA/210, PCT/US08/78633, "PCT International Search Report, " 2 pgs., Dec. 5, 2008.
Form PCT/ISA/237, PCT/US08/78633, "PCT Written Opinion of the International Searching Authority, " 6 pgs., Dec. 5, 2008.
Form PCT/ISA/220, PCT/US08/82147, "PCT Notification of Transmittal of The International Search Report and the Written Opinion of the International Searching Authority, or the Declaration, " 1 pg., Jan. 21, 2009.
Form PCT/ISA/210, PCT/US08/82147, "PCT International Search Report, " 2 pgs., Jan. 21, 2009.
Form PCT/ISA/237, PCT/US08/82147, "PCT Written Opinion of the International Searching Authority, " 13 pgs., Jan. 21, 2009.
Form PCT/ISA/220, PCT/US08/82149, "PCT Notification of Transmittal of The International Search Report and the Written Opinion of the International Searching Authority, or the Declaration, " 1 pg., Jan. 21, 2009
Form PCT/ISA/210, PCT/US08/82149, "PCT International Search Report, " 2 pgs., Jan. 21, 2009.
Form PCT/ISA/237, PCT/US08/82149, "PCT Written Opinion of the International Searching Authority, " 14 pgs. Jan., 21, 2009.
Form PCT/ISA/220, PCT/US08/75651, "PCT Notification of Transmittal of The International Search Report and the Written Opinion of the International Searching Authority, or the Declaration, " 1 pg., Nov. 28, 2008.
Form PCT/ISA/210, PCT/US08/75651, "PCT International Search Report, " 2 pgs., Nov. 28, 2008.
Form PCT/ISA/237, PCT/US08/75651, "PCT Written Opinion of the International Searching Authority, " 9 pgs., Nov. 28, 2008.
Form PCT/ISA/220, PCT/US08/85723, "PCT Notification of Transmittal of The International Search Report and the Written Opinion of the International Searching Authority, or the Declaration, " 1 pg., Mar. 20, 2009.
Form PCT/ISA/210, PCT/US08/85723, "PCT International Search Report, " 2 pgs., Mar. 20, 2009.
Form PCT/ISA/237, PCT/US08/85723, "PCT Written Opinion of the International Searching Authority, " 7 pgs., Mar. 20, 2009.
Form PCT/ISA/220, PCT/US08/85203, "PCT Notification of Transmittal of The International Search Report and the Written Opinion of the International Searching Authority, or the Declaration, " 1 pg., Feb. 27, 2009.
Form PCT/ISA/210. PCT/US08/85203, "PCT International Search Report, " 2 pgs., Feb. 27, 2009.
Form PCT/ISA/237, PCT/US08/85203, "PCT Written Opinion of the International Searching Authority, " 6 pgs., Feb. 27, 2009.
Form PCT/ISA/220, PCT/US08/75649, "PCT Notification of Transmittal of The International Search Report and the Written Opinion of the International Searching Authority, or the Declarartion, " 1 pg., Nov. 19, 2009
Form PCT/ISA/210. PCT/US08/75649, "PCT International Search Report, " 3 pgs., Nov. 19, 2009.
Form PCT/ISA/237, PCT/US08/75649, "PCT Written Opinion of the International Searching Authority, " 5 pgs., Nov. 19, 2009.
Technology Platform: SmartShirt + Eye-Tracking Innerscope Research, March 2007.
Office Action, issued by the United States Patent and Trademark Office in connection with U.S. Appl. No. 11/835,634, on Feb. 26, 2013, 24 pages.
Office Action, issued by the United States Patent and Trademark Office in connection with U.S. Appl. No. 11/804,555, on Mar. 6, 2013, 7 pages.
Notification of Rejection, issued by the Japanese Intellectual Property Office in connection with Japanese Application No. 2009-552660, on Mar. 13, 2013, 3 pages.

* cited by examiner

FIG. 5
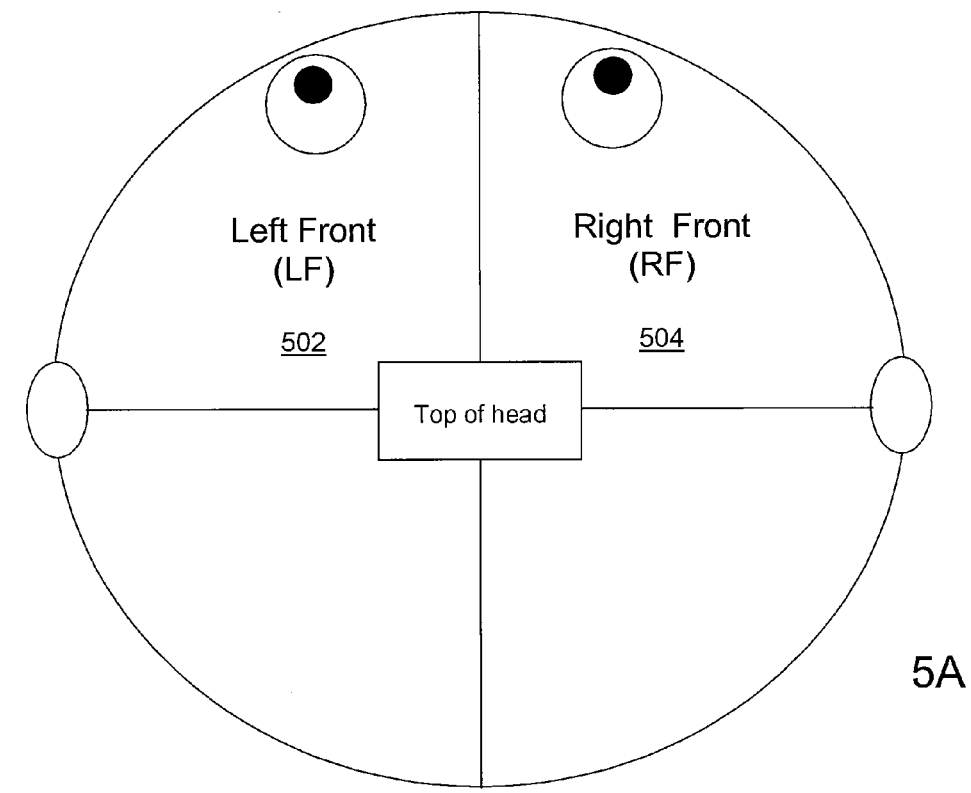
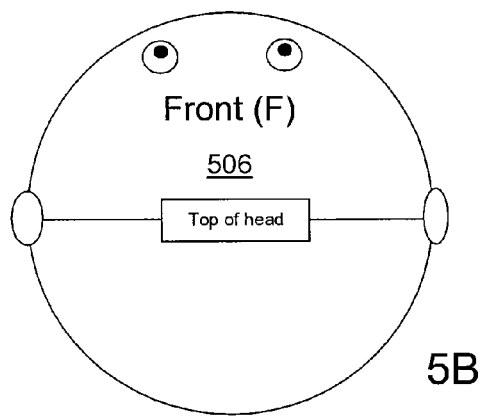
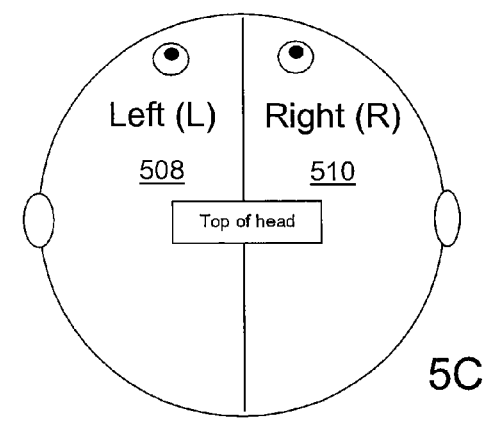

METHOD AND SYSTEM FOR MEASURING AND RANKING A POSITIVE OR NEGATIVE RESPONSE TO AUDIOVISUAL OR INTERACTIVE MEDIA, PRODUCTS OR ACTIVITIES USING PHYSIOLOGICAL SIGNALS

RELATED APPLICATIONS

This application claims priority to U.S. Provisional Patent Application No. 60/905,181, filed Mar. 7, 2007, and entitled "Method and system for measuring and ranking 'positive' or 'negative' response to audiovisual or interactive media, products or activities using physiological signals" by Hans C. Lee, et. al., which is incorporated herein by reference.

BACKGROUND

Creative people design interactive media, activities and products ("media") that stimulate individuals in positive or negative ways. Often times media are sold to consumers in highly competitive markets where the ability to stimulate positiveness or negativeness determines value. The creative people would like to know whether positiveness or negativeness is stimulated in order to maximize value by improving media to better stimulate individuals. If the value of the media is not maximized customers will purchase competing products which provide better stimulation. If competing products are sold, revenue will be lost as sales decline. A problem then is in providing accurate information about a response to stimulation by interactive media, activities, and products. Measuring the response requires creators of interactive media, activities and products to enter the minds of the target market.

In entering the human mind Researchers in Neurobiology, Psychophysiology, and Psychology found physiological signals emanating from the brain. Using the Electroencephalogram (EEG) researchers recorded the physiological signals though electrodes attached to the head. The physiological signals had four main components below 30 hertz. Frequencies between 1-4 hertz were delta waves ($\delta$), frequencies between 4 and 8 hertz were theta ($\theta$) waves, frequencies between 8-13 hertz were alpha ($\alpha$) brainwaves, and frequencies between 13 and 20 were beta ($\beta$) brainwaves. Researchers studied the mind using the EEG; however, a system and method for measuring and ranking positiveness or negativeness response was not made available. The amount that media positively or negatively stimulates individuals to was still unknown.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools, and methods that are meant to be exemplary and illustrative, not limiting in scope. In various embodiments, one or more of the above described problems have been reduced or eliminated, while other embodiments are directed to other improvements.

A novel technique measures a positiveness or negativeness response of an individual to a media as a valence value. The technique uses physiological signals emanating from the brain to gauge the valence response. A valence value is an objective measure of positiveness or negativeness response where a positive valence value represents positiveness and a negative valence value represents negativeness. Advantageously, the valence value could be centered at 0, readily identifying values greater than zero are positive, and values less than zero are negative, but it is not necessary to do so and another centering point could be used. Advantageously, a valence value could be used to rank different media. These media have appreciable events, e.g. in a live action football game a touchdown would be a generally positive event for the fans of the team scoring. Ranking can be as simple as calculating a valence value of each of a user's response to a first media and a second media and comparing the two valence values to see which is higher. The higher value relates to the media which has produced a more positive response in the individual. Further, groups of individuals can have a valence response that can be measured and aggregated to determine the overall population response to the media. This population view of the media can then be used to rank the media which is a novel use of physiological changes in response to media.

BRIEF DESCRIPTION OF THE DRAWINGS

Embodiments of the inventions are illustrated in the figures. However, the embodiments and figures are illustrative rather than limiting; they provide examples of the inventions.

FIG. 5A-C depict diagrams 500 of a top view of a head. FIG. 4A and divides the front of the head into left front and right front. FIG. 4B identifies the front of the head. FIG. 4C divides the head into a left and a right.

DETAILED DESCRIPTION

In the following description, several specific details are presented to provide a thorough understanding of embodiments of the invention. One skilled in the relevant art will recognize, however, that the invention can be practiced without one or more of the specific details, or in combination with other components, etc. In other instances, well-known implementations or operations are not shown or described in detail to avoid obscuring aspects of various embodiments of the invention.

A novel system and method for measures a "valence" response to interactive media, products or activities. The technique uses physiological signals emanating from the brain to gauge the valence response. A processing component collects the physiological signals through the physiological sensors and substantially concurrently assigns a valence value to the amount the individual is positively or negatively stimulated. "Substantially concurrently" means that the response is at the same time or near in time to the stimulation. There may be a delay in the response. Therefore, the valence value is calculated with the understanding that the response may be immediately following if not exactly at the same time with the stimulation.

In some embodiments, an exemplary way of calculating a valence value is to consider alpha asymmetry. Two useful physiological signals for calculating a valence value include alpha waves and theta waves. In an illustrative embodiment this calculation is accomplished via a formula designed to compare left and right alpha and or theta values. Other useful signals are emanated from the brain in the range of 1-100 Hz.

Figure 1:
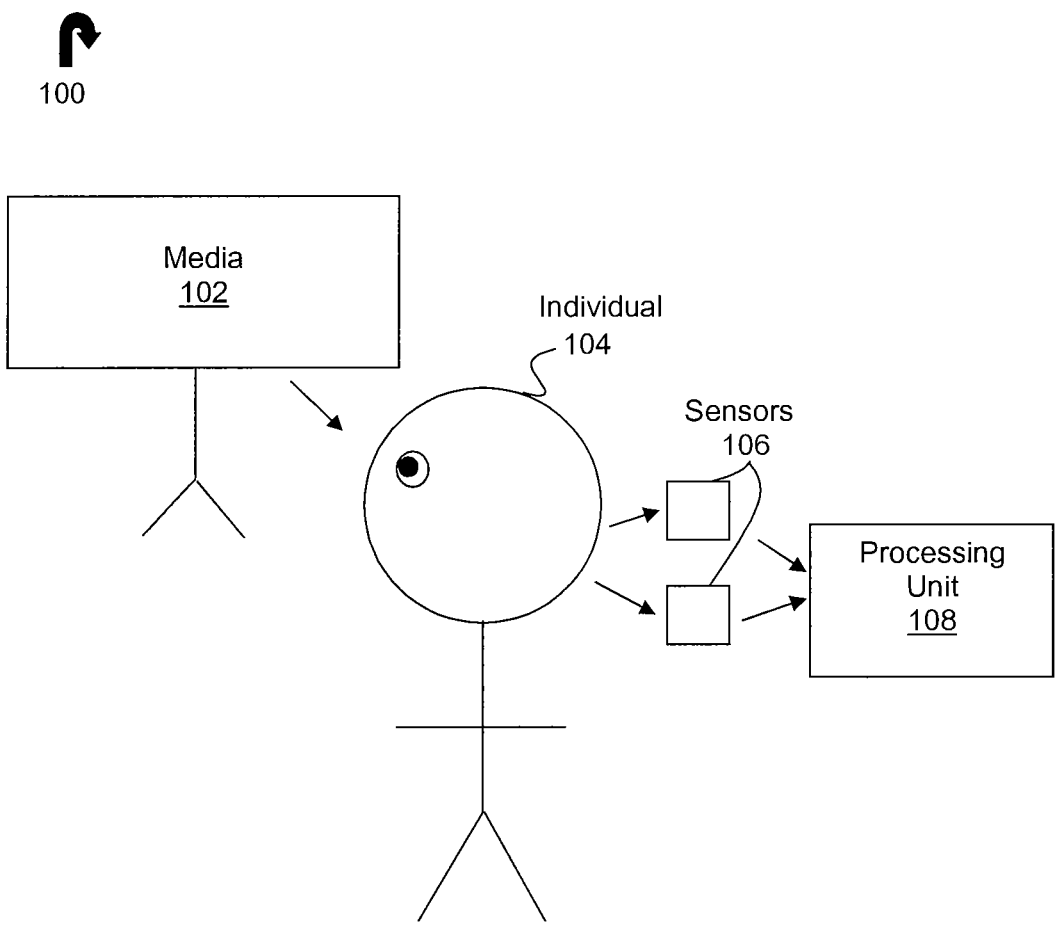
FIG. 1 is an illustration of an example of a system 100 for calculating a valence value.

FIG. 1 is an illustration of an example of a system 100 for calculating a valence value. Although this illustration depicts components as functionally separate, such depiction is merely for illustrative purposes. Those skilled in the art know that the components portrayed in this figure can be arbitrarily combined or divided into separate software, firmware and/or hardware components. Furthermore, such components, regardless of how they are combined or divided, can execute on the same computing device or multiple computing devices, and wherein the multiple computing devices can be connected by one or more networks.

In the example of FIG. 1, the system 100 includes media 102, individual 104, sensors 106, and processing component 108. As depicted, individual 104 is stimulated by media 102 while having his valence (positiveness/negativeness) is monitored by processing component 108 using sensors 106. Here the media can be one or more of a movie, a video a television program, a commercial, an advertisement, a video game, an interactive online media, a print, or any other media which could stimulate an individual. Sensors 106 could be one or more of an accelerometer, a blood oxygen sensor, a galvanometer, an electroencephalogram, an electromygraph, and any other physiological sensor.

Figure 2:
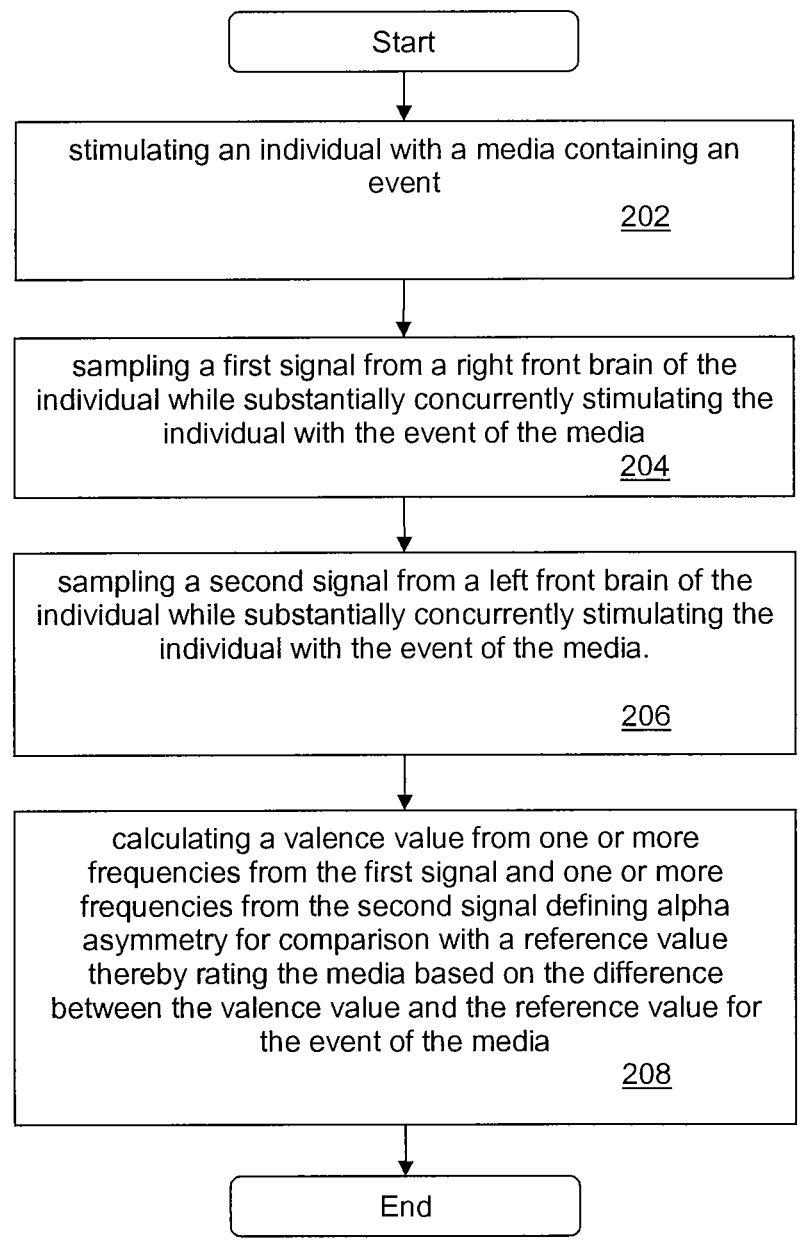
FIG. 2 depicts a flowchart 200 of an example of a method for calculating a valence value of an individual in response to stimulation by a media by considering alpha asymmetry.

FIG. 2 depicts a flowchart 200 of an example of a method for calculating a valence value of an individual in response to stimulation by a media by considering alpha asymmetry. The method is organized as a sequence of modules in the flowchart 200. However, it should be understood that these and other modules associated with other methods described herein may be reordered for parallel execution or into different sequences of modules. In the example of FIG. 2 flowchart 200 starts at module 202 with stimulating an individual with a media containing an event.

In the example of FIG. 2, the flowchart continues to module 204 with sampling a first signal from a right front brain while substantially concurrently stimulating the individual with the event of the media. The signal is sampled concurrently with the exposure to the media. There may be a delay in the response, therefore the signal is sampled with the understanding that the response may be immediately following if not exactly at temporal with the stimulation, thus it is substantially concurrent with the stimulation. The sampled signal will contain a range of different frequencies including alpha waves and theta waves. In the example of FIG. 2, the flowchart continues to module 206 with sampling a second signal from a left front brain while substantially concurrently stimulating the individual with the event of the media. This signal is also sampled substantially concurrently.

In some embodiments, the sampled signals are decomposed into the frequency domain. The fast Fourier transform (FFT), or wavelet analysis, both well known in the art of digital signal processing are used for decomposition. FFT is an efficient method of computing the discrete Fourier transform (DFT); DFT could be used as well as other methods of computing Fourier analysis. In the alternative, wavelet analysis could be used to divide the signal into its different frequency components so that they can be considered separately. Specifically, the Mexican hat wavelet, a morlet wavelet, a daubechies wavelet, a beta wavelet, and a coiflet wavelet would be useful for doing so. In the example of FIG. 2, the flowchart continues to module 208 with decomposing RF signals into the frequency domain. This is accomplished in the same manner as that of the $L_F$ signals.

In some embodiments, waves are separated from signals and stored into bins. In storing the frequencies from the signal, bins hold sampled signals from the frequency domain. A DFT bin can be defined by calculating an n point DFT. Specifically, n different sample values are created X(0) through X(n−1). With i being a value 0 to n−1, X(i) is a bin holding relevant sample values. The Alpha bin can hold anything between 8-13 hz, but not necessarily including all frequencies in that range. The Theta bin can hold anything between 4-8 hz, but does not have to include all frequencies. Similarly, delta and beta waves can be held in delta and beta bins. Additionally, the frequency profile can be adjusted to remove noise in the signal such as white noise or pink noise.

In the example of FIG. 2, the flowchart continues to module 208 with calculating a valence value from one or more frequencies from the first signal and one or more frequencies from the second signal defining alpha asymmetry for comparison with a reference value thereby rating the media based on the difference between the valence value and the reference value for the event of the media.

In some embodiments calculating a valence value is accomplished via a formula designed to compare left and right alpha and or theta values as selected from one of the formulas below. $\alpha_{RF}$ designates right frontal alpha, $\alpha_{LF}$ designates left frontal alpha, $\theta_{LF}$ designates left frontal theta, $\theta_{RF}$ designates right frontal theta, $\theta_L$ designates left theta, $\theta_R$ designates left theta, $\alpha_L$ designates left alpha $\alpha_R$ designates right alpha.

$$\boxed{\alpha_{RF} - \alpha_{LF}} \quad \boxed{\theta_{LF} - \theta_{RF}} \quad \boxed{\frac{\theta_L}{\alpha_L} - \frac{\theta_R}{\alpha_R}} \quad \boxed{\frac{(\theta_L - \alpha_L)/(\theta_L + \alpha_L)}{(\theta_R - \alpha_R)/(\theta_R + \alpha_R)}}$$

These example formulas are intended to be non-limiting. A number of different formulas would work and one of these formulas could be modified in the spirit of these teachings to create a formula that would suit a specific application.

In some embodiments, should valence be calculated in terms of negativeness, the following formulas could be used. The formulas use the same designations for alpha and theta as above.

$$\boxed{\alpha_{LF} - \alpha_{RF}} \quad \boxed{\theta_{RF} - \theta_{LF}} \quad \boxed{\dfrac{\theta_R}{\alpha_R} - \dfrac{\theta_L}{\alpha_L}} \quad \boxed{\dfrac{(\theta_R - \alpha_R)/(\theta_R + \alpha_R)}{(\theta_L - \alpha_L)/(\theta_L + \alpha_L)}}$$

These example formulas are intended to be non-limiting. A number of different formulas would work and one of these formulas could be modified in the spirit of these teachings to create a formula that would suit a specific application.

Figure 3:
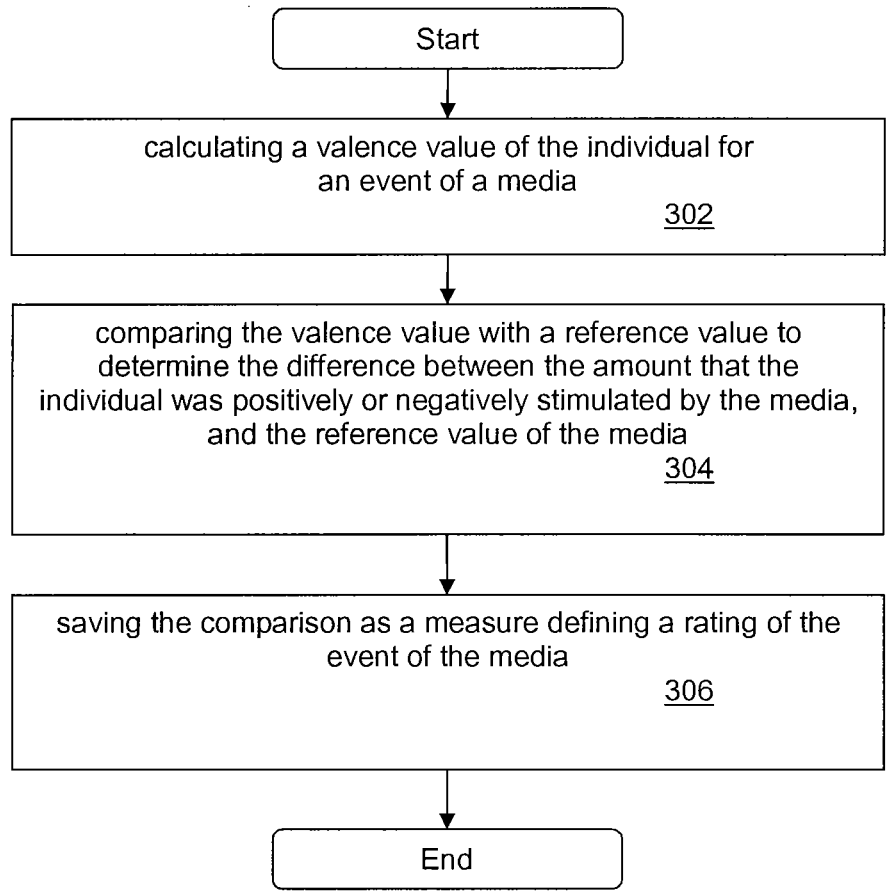
FIG. 3 depicts a flowchart 300 of an example of a method for rating media based on the amount that an individual is positively or negatively stimulated.

FIG. 3 depicts a flowchart 300 of an example of a method for rating media based on the amount that an individual is positively or negatively stimulated. The method is organized as a sequence of modules in the flowchart 300. However, it should be understood that these and modules associated with other methods described herein may be reordered for parallel execution or into different sequences of modules. In the example of FIG. 3 the flowchart starts at module 302 with calculating a valence value of the individual for an event of a media.

In the example of FIG. 3, the flowchart continues to module 304, comparing the valence value with a reference value to determine the difference between the amount that the individual was positively or negatively stimulated by the media, and the reference value of the media. This is also acquired in manner described in regard to FIG. 3.

In the example of FIG. 3, the flowchart continues to module 306 with saving the comparison as a measure defining a rating of the event of the media. This may utilize a formula which compares the alpha asymmetry of the right and left brain. In the example of FIG. 3, the flowchart continues to module 308 with calculating a second valence value from the second signal by considering alpha asymmetry in the individual's brain.

In some embodiments media are ranked based on their valence values. The media are compared with each other to determine which has a higher valence value, e.g. which one is more positively "liked," producing a more positive response. Advantageously, a plurality of media can be ranked against each other relative to an individual. Further individual events of a media could be ranked relative to each other, such as to produce the most positive scenes in a movie, or conversely, the more negative scenes in a movie so that they could be cut. As the values are numerical and objective, a system could be built on this technology that could rank media of disparate characteristics, such as comparing the positive response value of a television advertisement with a board game like chess relative to an individual. Further media can be compared based on a certain group in determining whether the group finds the media more positive than another media.

Figure 4:
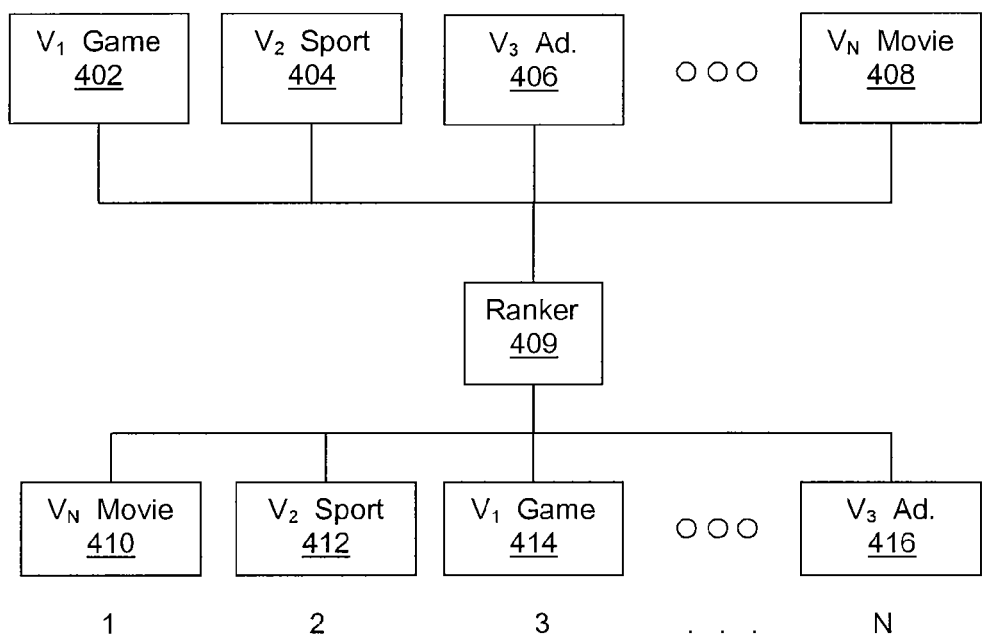
FIG. 4 depicts a diagram 400 ranking a plurality of media based on the valence values assigned to the media.

FIG. 4 depicts a diagram 400 ranking a plurality of media based on the valence values assigned to the media. Diagram 400 includes game 402, sport 404, ad. 406, movie 408, ranker 409, ranked movie 410, ranked sport 412, ranked game 414, and ranked ad. 416. In the example of FIG. 4, the unranked media game 402, sport 404, ad. 406, and movie 408 are later ranked in order of their ability to stimulate positiveness or negativeness as related to alpha asymmetry in the brain of an individual. Advantageously, a plurality of n different media could be ranked. The relative ranking of the different media could be accomplished by comparison relative to an individual or a group, and different statistical measures could be used to define the ranking as it suits the individual application.

FIG. 5A-C depicts top views 500 of a head identifying the front of the head and dividing the front of the head into left front and right front. FIG. 5A includes left front brain 502, and right front brain 505. FIG. 5B includes front brain 506. FIG. 5C includes left brain 508 and right brain 510. In the examples of FIG. 5A-C, the division of the brain is relevant to the understanding of the formulas used to calculate the valence values of the individual from the brainwaves of the individuals. Specifically identified are the parts of the brain the signals are collected from. In an illustrative example, right frontal alpha, $\alpha_{RF}$, is collected from right front brain 505. Left frontal alpha, $\alpha_{LF}$, is collected from left front brain 502. Right front theta, $\theta_{RF}$, is collected from right front brain 505. Left front theta, $\theta_{LF}$, is collected from left front brain 502. Right theta, $\theta_R$, is collected from right brain 510. Left theta, $\theta_L$, is collected from left brain 508. Left alpha, $\alpha_L$, is collected from left brain 508. Right alpha, $\alpha_R$ is collected from right brain 510.

Figure 6:
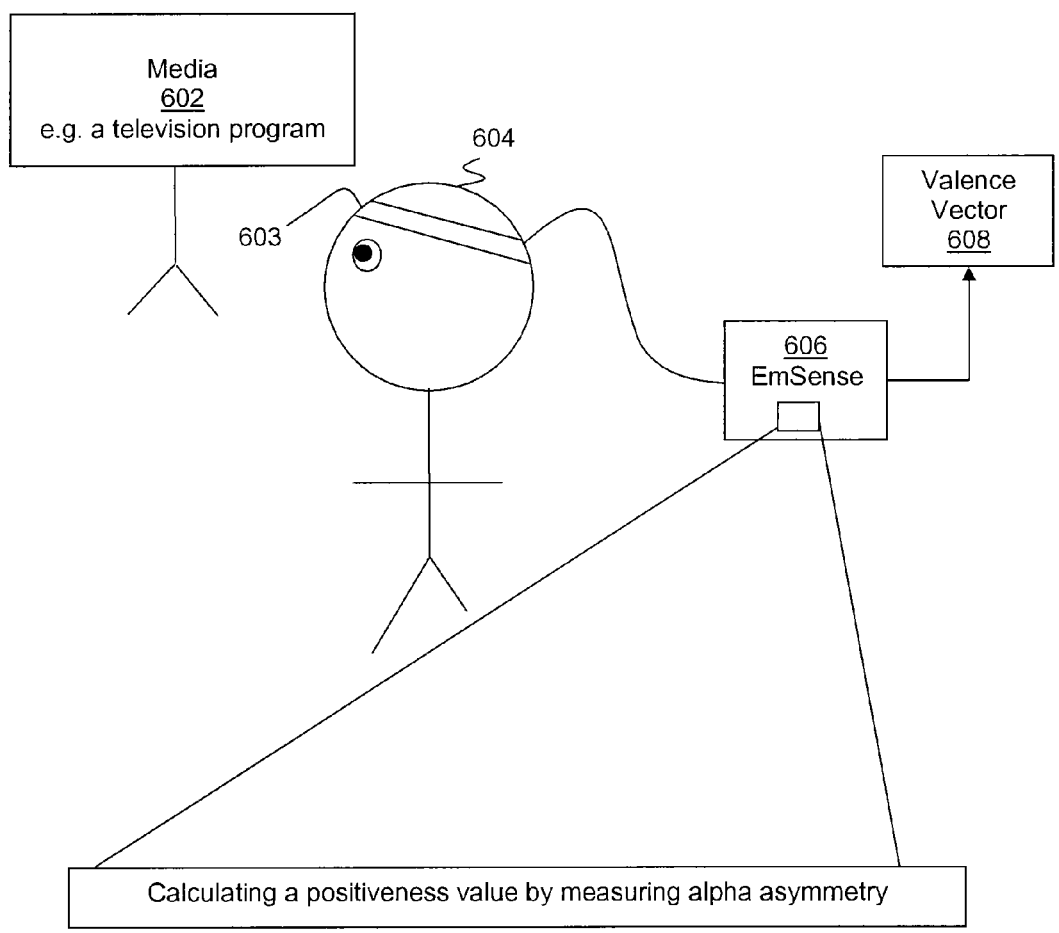
FIG. 6 depicts a diagram 600 of an example of stimulating an individual with a media while calculating a valence value.

FIG. 6 depicts a diagram 600 of an example of stimulating an individual with a media while calculating a valence value relating the individual's response to the media based on alpha asymmetry. Diagram 600 includes media 602, headset 603, individual 604, processing device 606, and valence vector 608. In the example of FIG. 6, individual 603 watches e.g. a television program, media 602, while having his valence level monitored by the processing device 606. Signals are collected from the head of the individual via headset 603. These signals are transmitted to processing device 606 for processing into a valence value.

In some embodiments an aggregate of a number of individual valence values derived from physiological responses is created determining a group response to a media. The aggregation can be by an average response for the number of individuals or by a higher ordered approximation.

Figure 7:
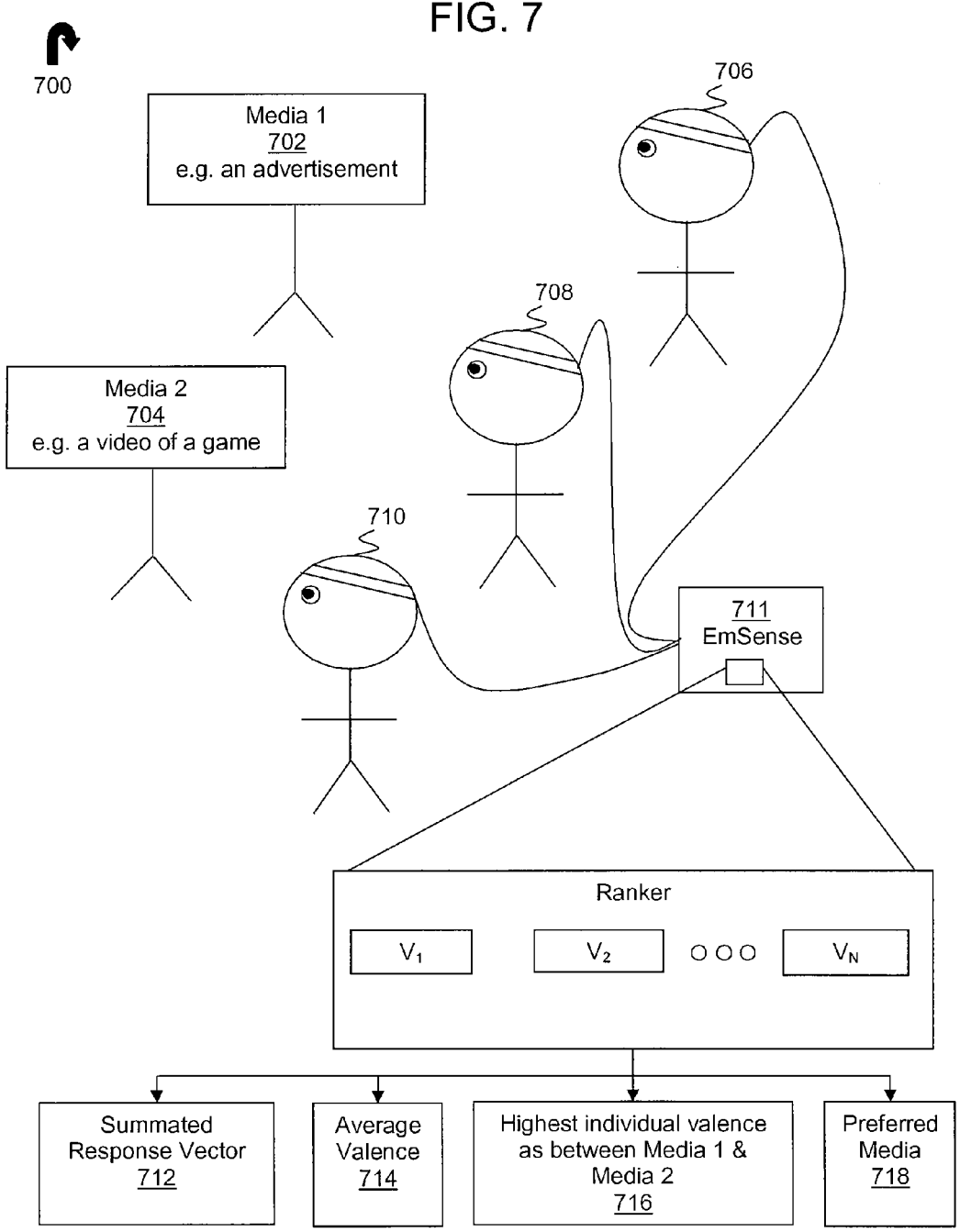
FIG. 7 depicts a diagram 700 of an example of stimulating a plurality of individuals with a media and calculating valence values and related values.

FIG. 7 depicts a diagram 700 of an example of stimulating a plurality of individuals with a media and calculating related valence values as stimulated by the media. Diagram 700 includes "media 1" 702, "media 2" 704, individuals 707, 708, and 710, processing device 711, summated response vector 712, average valence 714, highest valence 717, and preferred media 718. In the example of FIG. 7, the plurality of individuals 707, 708, and 710 are stimulated by the media and their collective valence levels are analyzed based on alpha asymmetry. In the case that a group is used to consider media, the summated response vector 712 would be a useful value in comparing media where the constant value would be the group of individuals, and their average valence would vary with the different media presented. The summated response vector 712 could be useful in determining how many persons responded with valence to a media.

In some embodiments, a valence value is aligned to a media by correlating an event occurring at a specific time to the valence value at that specific time. Aligning the valence values to the media provides useful information about the context of the valence values and why specific valence values are as high or low as they are. An individual response to the stimulus of a media may be broken down into events in time. In a non-limiting example a game could include an event identified as a referee signaling an erroneous foul. An individual having his valence level monitored while watching the game could be monitored for an increase in valence while the individual wonders "why did the referee signal a foul?" By correlating the valence value with the media, stimulus can be linked to positiveness or negativeness. Advantageously, this information can be used to improve the media by changing the media.

In some embodiments, an event is classified as a specific type of event by using a mathematical transform to compare the event with other events. Such mathematical transforms may include but are not limited to, an average, a first order derivative, a second order derivative, a polynomial approximation, a standard deviation from the mean, a standard deviation of derivatives from the mean, and profiles of the physiological responses, which can be implemented with convolution or other methods that takes into account one or more of: peaking in the middle, spiking in the beginning, being flat, etc.

In some embodiments a reference value is used to compare a user valence response to an event with a predetermined valence value of the event. The reference value could be anything developed for the purpose of providing a comparison value from which to determine a difference between the user's valence value and the event. Developers of media may create their own reference values. A reference value may be an ideal value i.e. a goal desired. A reference value could be the average of a number of different user valence values calculated solely for the purpose of developing a reference value from which to compare other individuals.

Figure 8:
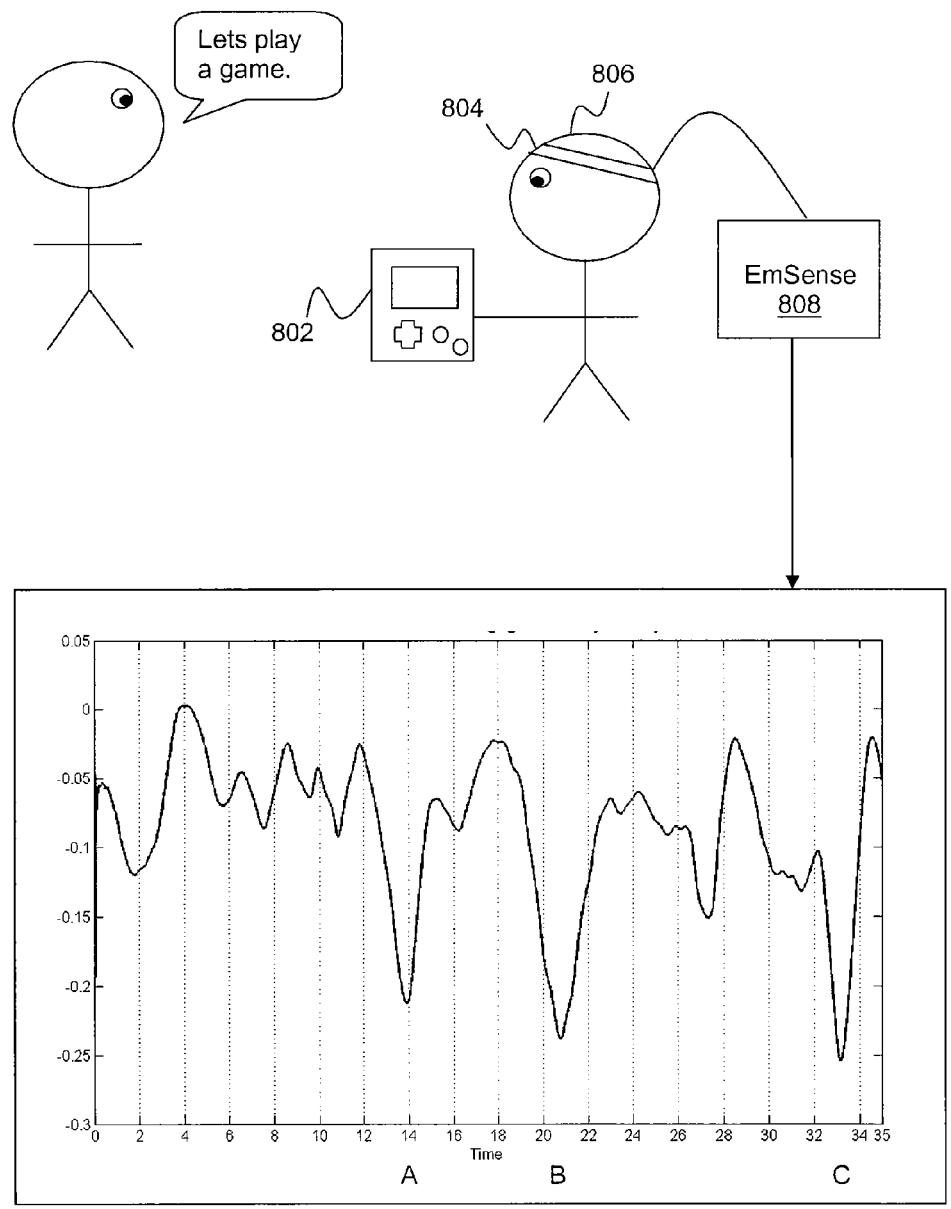
FIG. 8 depicts a diagram 800 of an experiment in which an individual is instructed to play a game, and the resultant valence values are calculated; key points in time are identified.

FIG. 8 depicts a diagram 800 of an experiment in which an individual is instructed to play a game, and the resultant valence values are calculated. Diagram 800 includes game 802, headset 804, individual 806, and processing device 808. In the example of FIG. 8, the individual 806 plays game 802, and the signal containing his brainwaves is collected via headset 804 and transmitted to processing device 808. Processing device 808 then calculates valence values and the resulting graph displays the changes in valence over time. At points A, B, and C, there are significant dips in valence over time. These are associated with negative points in time of the game.

In some embodiments a derivative of the valence value is calculated at a point in time to see the change in the valence over time. This value can be used to gauge whether a specific event occurring in time concurrently with or right before the point in time is related to the change in valence. Where a person experiences an event of the media which she likes, the derivative could be at least temporarily positive indicating an increasingly positive response to the event. This advantageous because it would allow the creators of media to identify events of media, e.g. a touchdown in a football game, which are desirable for producing positive responses. Similarly negative derivatives of the valence vector when correlated with events of the media can be also identified, e.g. losing a game. Although the example events may be linked obvious ways to positive and negative responses to events, there other events may not be so similarly obvious, such as the response an individual would have to a lesson in a training seminar, or a newly created cinematographic technique applied to a scene in a movie.

Figure 9:
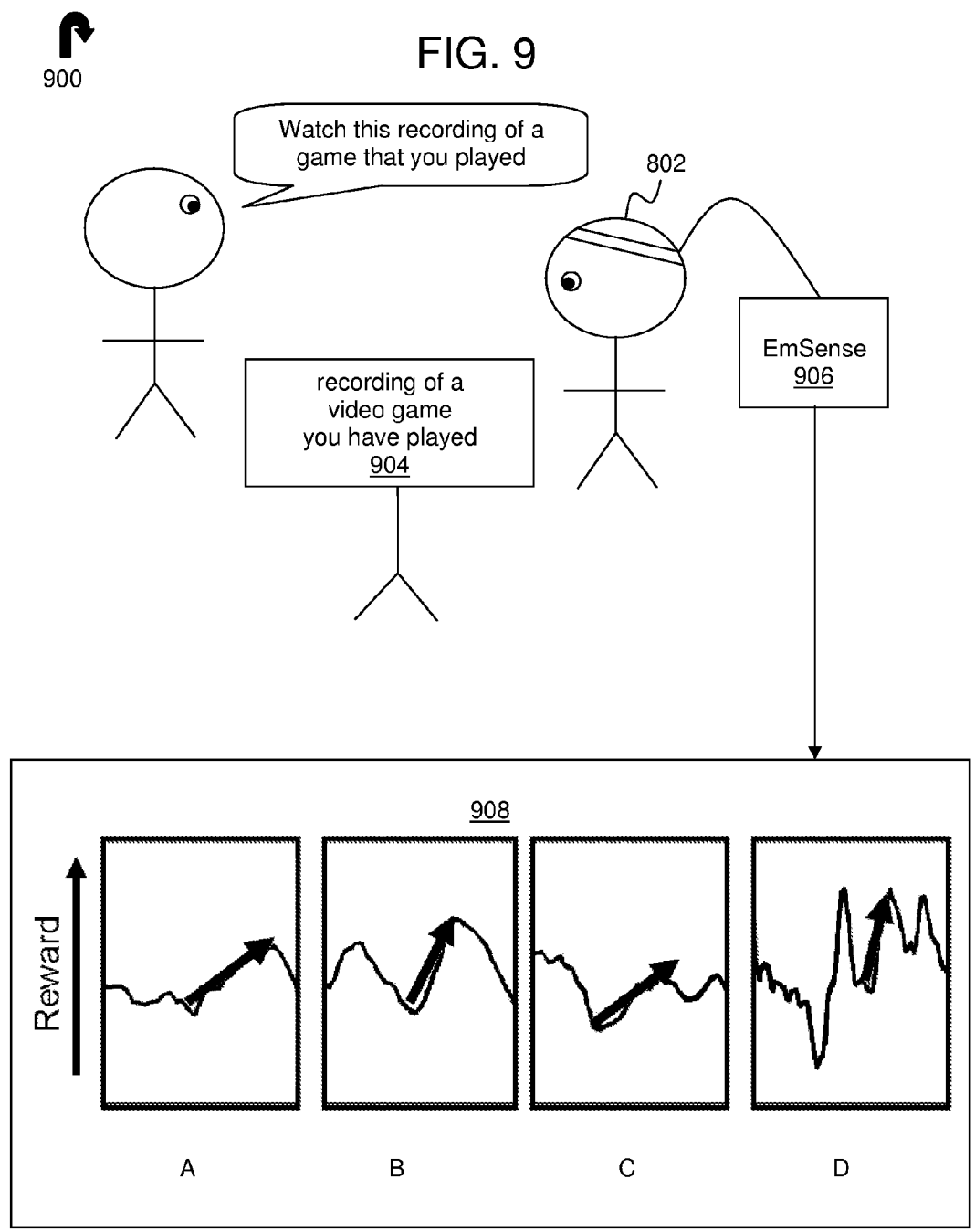
FIG. 9 depicts a diagram 900 of an experiment in which an individual views a video of a game which he recently played, and valence values are calculated from his brainwaves.

FIG. 9 depicts a diagram 900 of an experiment in which an individual views a video of a game which he recently played, and valence values are calculated from his brainwaves. FIG. 9 includes individual 902, recording of a video game 904, processing device 906, and graph 908. In the example of FIG. 9, the individual 902 views a recorded video of a game he previously played, re-living the experience of the game. Concurrently, his brainwaves are recorded and processed by processing device 906 which produces graph 908 of the valence over time. Certain point of increased valence A though D is associated with positive events in the game as shown by the positive valence. In the actual experiment, the individual confirmed that these were positive points of the game. The derivative as discussed in reference to FIG. 1 may be utilized to provide additional information; since a derivative mathematically produces a tangent line to a point on a curve, the derivative is well suited to providing lines indicating the direction of increase in positiveness or decrease in negativeness. At the points A through D, lines are drawn indicating positive derivatives identifying the increasing valence value relative to time.

In some embodiments, an integrated headset can be placed on a viewer's head for measurement of his/her physiological data while the viewer is watching an event of the media. The data can be recorded in a program on a computer that allows viewers to interact with media while wearing the headset.

Figure 10:
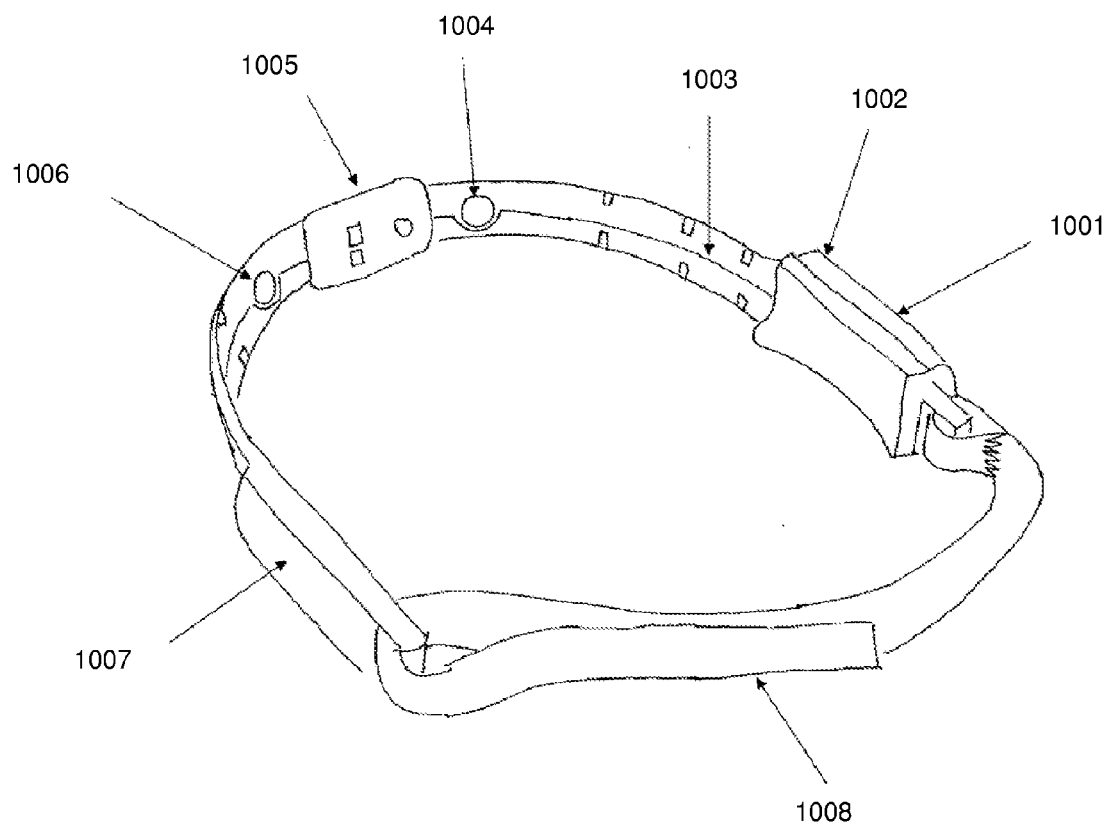
FIG. 10 depicts a diagram 1000 of a headset containing electrodes useful for collecting signals from a head of an individual.

FIG. 10 depicts a headset 1000 containing electrodes useful for collecting signals from a head of an individual. Headset 1000 includes processing unit 1001, three axis accelerometer 1002, silicon stabilization strip 1003, right EEG electrode 1004, heart rate sensor 1005, left EEG electrode 1006, battery module 1007, and adjustable strap 1008. Processing unit 1001 is a microprocessor that digitizes physiological data and can process the data into physiological responses that include but are not limited to thought, engagement, immersion, physical engagement, valence, vigor and others. A three axis accelerometer 1002 senses movement of the head. A silicon stabilization strip 1003 allows for more robust sensing through stabilization of the headset that minimizes movement. The right EEG electrode 1004 and left EEG electrode 1006 are prefrontal dry electrodes that do not need preparation to be used. Contact is needed between the electrodes and skin but without excessive pressure. The heart rate sensor 1005 is a robust blood volume pulse sensor positioned about the center of the forehead and a rechargeable or replaceable battery module 1007 is located over one of the ears. The adjustable strap 1008 in the rear is used to adjust the headset to a comfortable tension setting for many different head sizes.

It will be appreciated to those skilled in the art that the preceding examples and embodiments are exemplary and not limiting to the scope of the present invention. It is intended that all permutations, enhancements, equivalents, and improvements thereto that are apparent to those skilled in the art upon a reading of the specification and a study of the drawings are included within the true spirit and scope of the present invention. It is therefore intended that the following appended claims include all such modifications, permutations, and equivalents as fall within the true spirit and scope of the invention.

We claim:

1. A method comprising:
obtaining data representative of a first signal, the first signal gathered from a right side of a brain of an individual while the individual is substantially concurrently exposed to media, the first signal comprising a right alpha wave ($\alpha_R$) and a right theta wave ($\theta_R$);
obtaining data representative of a second signal, the second signal gathered from a left side of the brain of the individual substantially concurrently as the first signal is gathered, the second signal comprising a left alpha wave ($\alpha_L$) and a left theta wave ($\theta_L$);
using a processor to calculate a valence value using a formula comprising at least one of:

$(\theta_L/\alpha_L)-(\theta_R/\alpha_R)$, $([\theta_L-\alpha_L]/[\theta_L+\alpha_L])/([\theta_R-\alpha_R]/[\theta_R+\alpha_R])$, $(\theta_R/\alpha_R)-(\theta_L/\alpha_L)$, or $([\theta_R-\alpha_R]/[\theta_R+\alpha_R])/([\theta_L-\alpha_L]/[\theta_L+\alpha_L])$ comparing the valence value with a reference value to determine a difference; and
rating the media based on the difference.

2. The method of claim 1 further comprising aggregating multiple valence values from multiple individuals exposed to the media to form a valence response to the media.

3. The method of claim 1 further comprising decomposing the first signal and the second signal into a frequency domain using a fast Fourier transform or a wavelet analysis.

4. The method of claim 1 further comprising calculating a derivative of the valence value representative of a change in valence over time.

5. The method of claim 1 wherein the media comprises one or more of a television broadcast, a video game, an audiovisual advertisement, a board game, a card game, a live action event, a print advertisement or a web advertisement.

6. The method of claim 1 further comprising:
identifying a point in time corresponding to the valence value;
identifying an event of the media occurring substantially concurrently as the point in time;
correlating the valence value with the event; and
aligning the valence value to the media.

7. The method of claim 1 wherein the reference value comprises an average value of a plurality of previously calculated valence values of other individuals.

8. A system comprising:
a data collector to:
obtain data representative of a first signal, the first signal gathered from a right side of a brain of an individual while the individual is substantially concurrently exposed to media, the first signal comprising a right alpha wave ($\alpha_R$) and a right theta wave ($\theta_R$); and
obtain data representative of a second signal, the second signal gathered from a left side of a brain of the individual is substantially concurrently as the first signal is gathered, the second signal comprising a left alpha wave ($\alpha_L$) and a left theta wave ($\theta_L$); and
a processor to:
calculate a valence value using a formula comprising at least one of:

$(\theta_L/\alpha_L)-(\theta_R/\alpha_R)$, $([\theta_L-\alpha_L]/[\theta_L+\alpha_L])/([\theta_R-\alpha_R]/[\theta_R+\alpha_R])$, $(\theta_R/\alpha_R)-(\theta_L/\alpha_L)$, or $([\theta_R-\alpha_R]/[\theta_R+\alpha_R])/([\theta_L-\alpha_L]/[\theta_L+\alpha_L])$ compare the valence value with a reference value to determine a difference; and
rate the media based on the difference.

9. The system of claim 8, wherein the processor is to aggregate multiple valence values from multiple individuals exposed to the media to form a valence response to the media.

10. The system of claim 8, wherein the processor is to decompose the first signal and the second signal into a frequency domain using a fast Fourier transform or a wavelet analysis.

11. The system of claim 8, wherein the processor is to calculate a derivative of the valence value representative of a change in valence over time.

12. The system of claim 8 wherein the media comprises one or more of a television broadcast, a video game, an audiovisual advertisement, a board game, a card game, a live action event, a print advertisement or a web advertisement.

13. The system of claim 8, wherein the processor is to:
identify a point in time corresponding to the valence value;
identify an event of the media occurring substantially concurrently as the point in time;
correlate the valence value with the event; and
align the valence value to the media.

14. The system of claim 8 wherein the reference value comprises an average value of a plurality of previously calculated valence values of other individuals.

15. A tangible machine readable storage medium comprising instructions, which when executed, cause a machine to at least:
calculate a valence value based on a first signal and a second signal, the first signal gathered from a right side of a brain of an individual while the individual is substantially concurrently exposed to media, the first signal comprising a right alpha wave ($\alpha_R$) and a right theta wave ($\theta_R$), the second signal gathered from a left side of the brain of the individual substantially concurrently as the first signal is gathered, the second signal comprising a left alpha wave ($\alpha_L$) and a left theta wave ($\theta_L$), and wherein the Valence value is calculated using a formula comprising at least one of:

$(\theta_L/\alpha_L)-(\theta_R/\alpha_R)$, $([\theta_L-\alpha_L]/[\theta_L+\alpha_L])/([\theta_R-\alpha_R]/[\theta_R+\alpha_R])$, $(\theta_R/\alpha_R)-(\theta_L/\alpha_L)$, or $([\theta_R-\alpha_R]/[\theta_R+\alpha_R])/([\theta_L-\alpha_L]/[\theta_L+\alpha_L])$ compare the valence value with a reference value to determine a difference; and
rate the media based on the difference.

\* \* \* \* \*